(12) United States Patent
Akatsuka et al.

(10) Patent No.: US 8,093,416 B2
(45) Date of Patent: Jan. 10, 2012

(54) METHOD FOR PRODUCING FATTY ACID ALKYL ESTERS AND/OR GLYCERIN USING FAT OR OIL

(75) Inventors: Takeo Akatsuka, Osaka (JP); Masanori Nonoguchi, Ibaraki (JP); Tomoharu Oku, Osaka (JP)

(73) Assignee: Nippon Shokubai Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 12/744,235

(22) PCT Filed: Oct. 17, 2008

(86) PCT No.: PCT/JP2008/069290
§ 371 (c)(1),
(2), (4) Date: Jun. 4, 2010

(87) PCT Pub. No.: WO2009/066539
PCT Pub. Date: May 28, 2009

(65) Prior Publication Data
US 2010/0286420 A1 Nov. 11, 2010

(30) Foreign Application Priority Data
Nov. 22, 2007 (JP) ................................. 2007-303747

(51) Int. Cl.
*C07C 51/00* (2006.01)

(52) U.S. Cl. ......... 554/163; 502/241; 502/324; 568/858

(58) Field of Classification Search .................. 554/163; 502/241, 324; 568/858
See application file for complete search history.

(56) References Cited

U.S. PATENT DOCUMENTS 3,306,905 A 2/1967 Hall et al.
(Continued)

FOREIGN PATENT DOCUMENTS
EP 1681281 7/2006
(Continued)

OTHER PUBLICATIONS

Extended European Search Report issued in related European Application No. 08852458.2 dated May 17, 2011.

*Primary Examiner* — Deborah D Carr
(74) *Attorney, Agent, or Firm* — Connolly Bove Lodge & Hutz LLP

(57) ABSTRACT

The present invention has an object to provide the following method for producing fatty acid alkyl esters and/or glycerin and the following catalyst used in the production method. According to the production method, a fat or oil is reacted with an alcohol to give a fatty acid alkyl ester and/or glycerin suitably used in a food or fuel application, etc., with high efficiency, and complicated steps such as a step of recovering a catalyst can be simplified or omitted. According to the catalyst, an active metal component is not eluted even if the catalyst is used repeatedly or for a long period of time, and further, such a catalyst can maintain an excellent catalyst activity for a long time even in the presence of water and exhibit a high activity to both of transesterification of a glyceride contained in the fat or oil and esterification of free fatty acid. In addition, the catalyst can exhibit a high catalyst activity even in the presence of an impurity such as a free fatty acid (FFA) contained in the fat or oil.
The present invention is a method for producing fatty acid alkyl esters and/or glycerin including a step of bringing a fat or oil into contact with an alcohol in the presence of a catalyst, wherein the catalyst includes a manganese element and a trivalent metal element.

25 Claims, 14 Drawing Sheets

U.S. PATENT DOCUMENTS

| | | | |
|---|---|---|---|
| 5,908,946 A | 6/1999 | Stern et al. | |
| 2004/0087809 A1 | 5/2004 | Nakayama et al. | |
| 2005/0164880 A1 | 7/2005 | Gesenhues et al. | |
| 2007/0037994 A1 | 2/2007 | Canos et al. | |

FOREIGN PATENT DOCUMENTS

| | | |
|---|---|---|
| FR | 679998 | 4/1930 |
| FR | 2 752 242 | 2/1998 |
| KR | 10-415396 | 4/2002 |
| WO | WO-98/56747 | 12/1998 |
| WO | WO-2002/081607 | 10/2002 |
| WO | WO-2005/035479 | 4/2005 |
| WO | WO 2005035479 A1 * | 4/2005 |
| WO | WO-2006/088254 | 8/2006 |
| WO | WO-2008/133189 | 11/2008 |

* cited by examiner

METHOD FOR PRODUCING FATTY ACID ALKYL ESTERS AND/OR GLYCERIN USING FAT OR OIL

CROSS-REFERENCE TO RELATED APPLICATION(S)

The present application claims priority to Japanese Patent Application No. 2007-303747 filed Nov. 22, 2007, entitled "METHOD FOR PRODUCING FATTY ACID ALKYL ESTERS AND/OR GLYCERIN USING FAT OR OIL". The contents of that application are incorporated herein by reference in their entirely.

TECHNICAL FIELD

The present invention relates to a method for producing fatty acid alkyl esters and/or glycerin. More specifically, the present invention relates to a method for producing fatty acid alkyl esters and/or glycerin useful for fuels, foods, cosmetics, pharmaceuticals and the like purposes. Further, the present invention relates to a catalyst used in the production method.

BACKGROUND ART

Fatty acid alkyl esters derived from vegetable oils are used as cooking oil and, in addition, used in such fields as cosmetics and pharmaceuticals. In recent years, attention has been paid to uses as additives to fuels such as gas oil. For example, fatty acid alkyl esters are added to gas oil in an amount of several percents as vegetable-derived biodiesel fuel for reducing emission of $CO_2$. Glycerin is mainly used as a raw material for nitroglycerin and is further used as a raw material for alkyd resins, or for pharmaceuticals, foods, printing inks, cosmetics and the like. As a method for producing such fatty acid alkyl esters and/or glycerin, transesterification of alcohols with triglyceride which is a main component of fats and oils is known.

In carrying out such a production method on a commercial scale, a homogenous alkaline catalyst is generally used.

However, the method needs complicated steps in order to separate and remove the catalyst from the reaction system. Also, the alkaline catalyst causes saponification of free fatty acids contained in the fats and oils. Therefore, soaps are produced as a byproduct, which needs a step of washing the produced soaps with large amounts of water. In addition, the yield of fatty acid alkyl esters decreases due to the emulsifying effect of the soaps and, in certain instances, the subsequent glycerin purification process becomes complicated.

Korea Patent No. 415396 discloses, as a prior art of producing glycerin and/or a fatty acid alkyl ester using a natural fat or oil, a method for producing a fatty acid ester, including the steps of: bringing a plant and animal fat or oil into contact with an alcohol equal to 2 to 40 times the fat or oil in molar ratio at 60 to 200° C. for 0.5 to 18 hours in the presence of a metal oxide catalyst that is magnesium oxide (MgO) or manganese oxide (MnO) which accounts for 0.1 to 10% by weight relative to the fat or oil, thereby preparing a mixture of a fatty acid ester with glycerin; and separating the mixture into each component. WO 1998/56747 discloses a method of performing transesterification of triglyceride derived from a plant or an animal with mono- or polyalcohol in the presence of an heterogeneous solid catalyst, wherein aluminum, chromium, magnesium, zinc, calcium, copper, manganese, or a mixed oxide derived from them is used as the heterogeneous solid catalyst.

However, these technologies have still room for contrivance in order to more improve a life of the catalyst, thereby suppressing a reduction in activity of the catalyst or purity of a generated product due to leaching of an active component of the catalyst. Further, according to these technologies, free fatty acid (FFA) and/or water contained in a starting material further reduces the life of the catalyst. Therefore, these technologies also have room for contrivance in order to suppress the reduction in activity in such a case.

WO 2005/35479 discloses the following production method of a fatty acid monoester and a polyalcohol, wherein a polyalcohol is transesterified with a compound selected from the group consisting of an animal fat or oil, a plant fat or oil, and a fatty acid methyl ester, thereby producing a fatty acid monoester and a polyalcohol, wherein a solid base catalyst is used as the catalyst, and the solid base catalyst is selected from the group consisting of a metal oxide of monovalent and trivalent elements, a metal oxide of divalent and trivalent elements, and a mixture thereof. According to this technology, a fatty acid monoester and a polyalcohol are produced using a solid base catalyst including a specific element. However, this technology has a problem in that a catalyst component leaches out during the reaction, which shortens the life of the catalyst. Therefore, there is room for contrivance in order to suppress the reduction in activity, caused by the leaching of the active component.

In a conventional method for solving the above-mentioned problems, in order to suppress a reduction in purity of a product due to reduction in yield, a catalyst whose activity has been reduced can be frequently exchanged for a new catalyst. However, an increase in the number of times for exchanging the catalyst is not preferable for industrial production. This is because costs on the catalyst are increased and because productivity is reduced if a production apparatus is stopped for exchange of catalyst. Further, in order to remove an active component which has been leached from a generated product, complicated purification steps such as rinsing and distillation are needed. Therefore, a production apparatus needs to be provided with an additional step. In such points, the conventional methods are not preferable in terms of industrial production. Accordingly, in the above-mentioned catalyst an active component needs to hardly leach. Further, the catalyst needs to maintain an excellent catalyst activity for a long time even if in the presence of water and an impurity such as free fatty acid (FFA). In these points, the catalyst has room for contrivance.

DISCLOSURE OF THE INVENTION

Problem to be Solved by the Invention

The present invention was made in view of the above-mentioned state of the art. The present invention has an object to provide the following production method of fatty acid alkyl esters and/or glycerin. Further, the present invention also has an object to provide the following catalyst used in the production method. That is, according to the production method, a fat or oil is reacted with an alcohol to give a fatty acid alkyl ester and/or glycerin suitably used in a food or fuel application, etc., with high efficiency, and complicated steps such as a step of recovering a catalyst can be simplified or omitted. In addition, according to the catalyst, an active metal component is not leached even if the catalyst is used repeatedly or for a long period of time, and further, such a catalyst can maintain an excellent catalyst activity for a long time even in the presence of water and exhibit a high activity to both of transesterification of a glyceride contained in the fat or oil and esterification of free fatty acid. In addition, the catalyst can exhibit a high catalyst activity even in the presence of an impurity such as a free fatty acid (FFA) contained in the fat or oil.

Means for Solving the Problem

The present inventors made various investigations on a method for producing fatty acid alkyl esters and/or glycerin. The inventors noted that a method for producing fatty acid alkyl esters and/or glycerin by bringing a fat or oil into contact with an alcohol in the presence of a solid catalyst is industrially useful. Then, the inventors made various investigations on a catalyst used in such a process. Then, the inventors found the following. According to a catalyst including a manganese element and a trivalent metal element, leaching of an active metal component is more sufficiently suppressed, and a life of the catalyst is sufficiently long. Further, the catalyst can maintain a high activity even in the presence of a free fatty acid (FFA) contained in the fat or oil, a mineral acid, a metal component, and water. Further, the catalyst does not dissolve the starting material alcohol. As a result, the above-mentioned problems have been admirably solved.

In addition, the inventors found the following. If the trivalent metal element is an oxide, the effect of maintaining a high activity for a longtime can be more remarkably exhibited regardless of existence of water in the starting material. Further, this effect is much more remarkably exhibited if the catalyst includes an aluminum oxide as the oxide of the trivalent metal element. The catalyst simultaneously exhibits the above-mentioned effects at a high level, which is a problem those skilled in the art had not solved for a long time. Only the present invention has solved the problem successfully.

That is, the present invention relates to a method for producing fatty acid alkyl esters and/or glycerin, the method including a step of bringing a fat or oil into contact with an alcohol in the presence of a catalyst, wherein the catalyst includes a manganese element and a trivalent metal element.

The present invention also relates to a catalyst for producing fatty acid alkyl esters and/or glycerin, used in the method for producing fatty acid alkyl esters and/or glycerin.

The present invention is mentioned below in more detail.

According to the production method of fatty acid alkyl esters and/or glycerin of the present invention, a fat or oil is brought into contact with an alcohol in the presence of a catalyst including a manganese element and a trivalent metal element. According to the production method of the present invention, due to use of the catalyst including a manganese element and a trivalent metal element, esterification reaction and transesterification reaction can be simultaneously performed, and further a high catalyst activity is exhibited. Therefore, a fatty acid alkyl ester and/or glycerin can be produced with high yield and high selectivity. In addition, leaching of an active component of the catalyst can be sufficiently suppressed and the life of the catalyst is improved. Therefore, steps of recovering the catalyst can be remarkably simplified or omitted, and further the catalyst can be used for the reaction repeatedly. Hence, recycling efficiency of the catalyst is more improved, and utility costs and equipment costs are significantly reduced. Further, the catalyst-related costs can be reduced, and stable and long-term production is permitted, for example. Particularly in the presence of a free fatty acid (FFA) contained in the fat or oil, a mineral acid, a metal component, or water, the catalyst generates no soap as a byproduct and further exhibits high catalyst activity without being influenced by these impurities.

It is preferable that the trivalent metal element is an oxide of the trivalent metal element. If the trivalent metal element is an oxide, the effects of the present invention are more remarkably exhibited. If the trivalent metal element is an oxide, the catalyst of the present invention includes a manganese element and a trivalent metal element that is an oxide.

In this case, the manganese element and the trivalent metal element may be the same or different compounds. Also, in the present invention, "the catalyst including a manganese compound and an oxide of a trivalent metal element" may includes the manganese element and the trivalent metal element as the same compounds or different compounds.

One or more species may be used as the catalyst of the present invention. The catalyst may contain impurities and other components produced in the catalyst preparation step unless effects of the present invention are sacrificed. Another catalyst may be used in combination of the above-mentioned catalyst, but it is preferable that the catalyst of the present invention includes, as a main component, the above-mentioned catalyst including a manganese element and a trivalent metal element. It is preferable that the total amount of the catalyst including a manganese element and a trivalent metal element is 50% by weight or more relative to 100% by weight of the entire catalyst of the present invention. The total amount thereof is more preferably 80% by weight or more, and still more preferably 85% by weight or more, and particularly preferably 90% by weight or more, and most preferably 95% by weight or more.

The catalyst including a manganese element and a trivalent metal element exhibits a catalyst activity of the catalyst of the present invention. Accordingly, if the above-mentioned catalyst satisfies the above-mentioned ratio by weight and the like, the effects of the present invention can be more remarkably exhibited.

A free fatty acid (FFA) and/or water generally exist in the above-mentioned fat or oil. Further, the fat or oil includes a mineral acid which is used to remove an impurity derived from a natural fat or oil, a metal component derived from a natural fat or oil, and an impurity such as sterol. Thus, according to the embodiment of the present invention, the reaction system generally includes a mineral acid, a metal component, sterol, phospholipid, water, free fatty acid (FFA), and the like. According to such an embodiment, the embodiment in which a manganese element and a trivalent metal element are used is preferable.

The catalyst of the present invention can naturally maintain high catalyst activity under various reaction conditions. Therefore, the catalyst can be preferably used even if the reaction system is substantially free from a free fatty acid (FFA) and/or water, or even if the reaction system is not substantially influenced by a free fatty acid (FFA) and/or water.

Examples of the above-mentioned trivalent metal element include aluminum, gallium, indium, thallium, scandium, yttrium, vanadium, chromium, iron, cobalt, and lanthanoid. One or more species of them may be used. Among these, aluminum is preferable as the trivalent metal element. If the trivalent metal element is an oxide of the trivalent metal element is an aluminum oxide, the catalyst is advantageous in terms of stability.

Thus, according to the above-mentioned catalyst, it is one of the preferable embodiments of the present invention that the trivalent metal oxide is an aluminum oxide.

The manganese element exists in the above-mentioned catalyst in the form of a simple substance, an alloy, a complex, an organic metal, a salt, a halide, a sulfide, a cyanide, and an oxide. Among these, it is preferable that the manganese exists in the catalyst in the form of an oxide. If manganese exists as an oxide, the catalyst is advantageous in terms of stability.

Thus, according to the catalyst, it is one of the preferable embodiments of the present invention that the manganese element is a manganese oxide.

This oxide is in the form of a single oxide, a composite oxide, or a mixed oxide. The single oxide is an oxide which includes one species of atom other than oxygen in one crystalline structure. The composite oxide is an oxide which includes two or more different species of atoms other than oxygen in one crystalline structure. The mixed oxide is a mixture of two or more species of a single oxide and/or a composite oxide.

A mixture of a manganese composite oxide with a single oxide of a trivalent metal element corresponds to the mixed oxide in the present description. An oxide including $MnTiO_3$ and $Al_2O_3$ is mentioned as such a mixed oxide, for example.

The above-mentioned manganese oxide in the form of a single oxide is a single oxide represented by $MnO_x$ (in the formula, x is the number of 1 or more and 7/2 or less). Preferable examples of the above-mentioned single oxide of manganese include $MnO$, $MnO_{4/3}$, $MnO_{3/2}$, $MnO_2$, and $MnO_{7/2}$. More preferable examples thereof include $MnO$, $MnO_{4/3}$, $MnO_{3/2}$, and $MnO_2$. $MnO_{4/3}$ used herein means $Mn_3O_4$; $MnO_{3/2}$ means $Mn_2O_3$; and $MnO_{7/2}$ means $Mn_2O_7$.

The above-mentioned manganese oxide in the form of a composite oxide may be crystalline or amorphous one. A crystalline composite oxide of manganese is preferably used, and an oxide including manganese and a metal element other than manganese in a crystal lattice is preferable. Examples of the metal element other than manganese include a titanium element, a cobalt element, a nickel element, a copper element, a zinc element, a niobium element, and a lanthanoid element. One or more species are preferable.

The above-mentioned aluminum oxide may be a single oxide of aluminum or a composite oxide of aluminum and an element other than manganese. The single oxide of aluminum is a compound represented by $Al_2O_3$. This oxide may be a single oxide of aluminum in α, γ, δ, η, θ, or κ crystalline form or a single oxide of amorphous aluminum. A single oxide of aluminum in α or γ crystalline form or amorphous aluminum is preferable in view of stability.

If the aluminum oxide is a composite oxide of aluminum and an element other than manganese, examples of the element forming the composite oxide together with aluminum include tetravalent metal elements such as zirconium, hafnium, tin, lead, silicon, germanium, and titanium; divalent metal elements such as zinc; and metalloid elements. Among these, zirconium, silicon, and titanium are preferable.

The above-mentioned other components included in the catalyst of the present invention are not especially limited unless the function of the catalyst is sacrificed. Tetravalent metal elements such as zirconium, hafnium, tin, lead, silicon, germanium, and titanium; divalent metal elements such as zinc; and metalloid elements are mentioned.

According to the above-mentioned catalyst, it is one of the preferable embodiments of the present invention that the catalyst is a mixed oxide and/or a composite oxide of a manganese oxide and an aluminum oxide. If the catalyst is in accordance with such an embodiment, the following effects can be more remarkably exhibited: the active component of the catalyst is hard to be leached and the excellent catalyst activity can be maintained for a long time in the presence of impurities such as water and a free fatty acid (FFA). Attributed to these effects, if this catalyst is used in a fixed bed continuous flow reactor, the reaction can be continuously performed for a long period of time. Therefore, such a catalyst is extremely advantageous industrially.

Examples of the above-mentioned mixed oxide of the manganese oxide and the aluminum oxide are shown below. A single oxide of manganese and a single oxide of aluminum; a composite oxide of manganese and a single oxide of aluminum; a single oxide of manganese and a composite oxide of aluminum; and a composite oxide of manganese and a composite oxide of aluminum. Among these, a mixed oxide of a single oxide of manganese and a single oxide of aluminum, or a mixed oxide of a single oxide of manganese and a composite oxide of aluminum is preferable.

If the above-mentioned catalyst is a mixed oxide of a manganese oxide and an aluminum oxide, the catalyst can be obtained by supporting a manganese compound on an aluminum compound and then calcined. Thus-obtained catalyst is in accordance with a preferable embodiment of the present invention.

An aluminum compound is impregnated with an aqueous solution of a manganese compound, thereby supporting a manganese compound on an aluminum compound. In this case, an aluminum oxide or hydroxide in the form of powder or particle as the aluminum compound is impregnated with an aqueous solution of a manganese compound. Manganese nitrate, manganese sulfate, manganese chloride, and manganese acetate can be used as the manganese compound which can be impregnated with an aluminum compound. It is preferable that the compound obtained by such an impregnation supporting manner is dried and subjected to a calcination treatment. After the calcination treatment, a mixed oxide of a manganese oxide and an aluminum oxide is obtained. Such a preparation method of the mixed oxide catalyst is also in accordance with a preferable embodiment of the present invention.

It is preferable that the above-mentioned calcination step is performed as follows, for example. The temperature for calcination is preferably 400° C. or more and 1500° C. or less. If the temperature is less than 400° C., a composite oxide might be insufficiently obtained. If it is more than 1500° C., a catalyst surface area might not be sufficient, which fails to produce fatty acid alkyl esters and/or glycerin with high efficiency. The temperature is more preferably 600° C. or more and 1500° C. or less, and still more preferably 600° C. or more and 1300° C. or less.

The calcination time is preferably 30 minutes or more and 24 hours or less, and more preferably 1 hour or more and 12 hours or less, and still more preferably 2 hours or more and 8 hours or less, and particularly preferably 3 hours or more and 7 hours or less.

The calcination is preferably performed under air, nitrogen, argon, oxygen, and the like atmosphere. More preferably, the calcination is performed under air atmosphere.

If the above-mentioned catalyst is a composite oxide of a manganese oxide and an aluminum oxide, examples of such a composite oxide include $MnAl_2O_4$ and $Mn_2AlO_4$. Such a catalyst can be produced by powder-mixing manganese carbonate with aluminum oxide and calcinating the mixture. Thus-obtained catalyst is in accordance with a preferable embodiment of the present invention.

It is preferable that the above-mentioned calcination step is performed as follows, for example. The calcination temperature is preferably 500° C. or more and 1500° C. or less, for example. If the temperature is less than 500° C., a composite oxide might be insufficiently obtained. If it is more than 1500° C., a catalyst surface area might not be sufficient, which fails to produce fatty acid alkyl esters and/or glycerin with high efficiency. The temperature is more preferably 800° C. or more and 1500° C. or less.

The weight ratio of the manganese oxide to the aluminum oxide, constituting the above-mentioned catalyst, is preferably 200:1 to 1:200. The weight ratio is more preferably 10:1 to 1:100, and still more preferably 3:1 to 1:50. Without these ranges, the effect attributed to the combination use of the manganese with the trivalent metal element might not be sufficiently exhibited. In the present invention, aluminum is preferably used as the trivalent metal element. It is preferable that the above-mentioned weight ratio is satisfied between the manganese oxide and the aluminum oxide.

According to the production method of the present invention, it is preferable that the catalyst has insolubility to a fat or oil, an alcohol, and a product (fatty acid alkyl esters, glycerin and the like) under reaction conditions (hereinafter referred also to as "insoluble catalyst"). A fat or oil is brought into contact with an alcohol in the presence of the catalyst and then, the alcohol is removed by evaporation in the absence of the catalyst. Then, the reaction mixture will separate into two phases as the reaction proceeds: one phase (ester phase) mainly containing a fatty acid alkyl ester; the other phase (glycerin phase) mainly containing glycerin. In this case, both phases contain the alcohol, and as a result, the phase-separation becomes insufficient. If the alcohol is removed by evaporation in the absence of the catalyst, the mutual solubility between the upper phase mainly containing fatty acid alkyl esters and the lower phase mainly containing glycerin decreases, which improves the separation of fatty acid alkyl esters from glycerin. Hence, a high-purity fatty acid alkyl ester and glycerin, which are products, can be obtained. At this time, if the active metal component of the catalyst leaches out, a reverse reaction proceeds in the above-mentioned step and thereby the yield of fatty acid alkyl esters decreases because a transesterification is a reversible reaction. As mentioned above, the phase separation after evaporating the alcohol from the reaction mixture in the absence of the catalyst allows easy purification and improved yield in the production method of fatty acid alkyl esters and/or glycerin. That is, according to one of the preferable embodiments of the present invention, the production method includes a step of bringing a fat or oil in contact with an alcohol in the presence of the catalyst, wherein the catalyst is insoluble to the fat or oil, the alcohol, and the product (fatty acid alkyl esters, glycerin and the like) under reaction conditions, and the alcohol is removed by evaporation in the absence of the catalyst before an ester phase and a glycerin phase, which are a reaction liquid, are separated from each other. Furthermore, addition of water in minute amounts further improves the separation of the fatty acid alkyl ester from the glycerin and the purification of the fatty acid alkyl ester and the glycerin.

The phrase "in the absence of the catalyst" means that an insoluble solid catalyst is hardly contained and the reaction liquid has 1000 ppm or less of a total concentration of active metal components leached from the catalyst. The "active metal component leached" means a metal component derived from the insoluble solid catalyst which is leached into the reaction liquid and capable of serving as a homogeneous catalyst with a catalytic activity in a transesterification and/or esterification under operation conditions. If more than 1000 ppm of the active metal component is leached into the reaction liquid, the reverse reaction might be insufficiently suppressed in the above-mentioned step of evaporating the alcohol. As a result, load of utility in the production can be insufficiently reduced. The concentration is preferably 800 ppm or less, and more preferably 600 ppm or less, and still more preferably 300 ppm or less. Most preferably, the reaction liquid substantially contains no active metal component.

The leaching amount of the above-mentioned active metal component of the catalyst in the reaction liquid can be determined by subjecting the reaction liquid as it is to fluorescent X-ray spectroscopy (XRF). A smaller leaching amount is preferably determined by an inductively coupled plasma (ICP) emission spectrometry.

If a catalyst including a manganese element and a trivalent metal element is used as the above-mentioned catalyst, as mentioned above, such a catalyst has the following characteristics: permitting the esterification and transesterification reaction simultaneously; free from influences from the mineral acid or the metal component contained in the fat or oil; and causing no decomposition of the alcohol. Therefore, fatty acid alkyl esters and/or glycerin can be produced with high efficiency by the production method of the present invention.

The method for producing fatty acid alkyl esters and/or glycerin according to the present invention includes a step of bringing a fat or oil into contact with an alcohol in the presence of a catalyst.

In the above-mentioned contacting step, as shown in the following formula, a transesterification reaction of triglyceride with methanol gives a fatty acid methyl ester and glycerin.

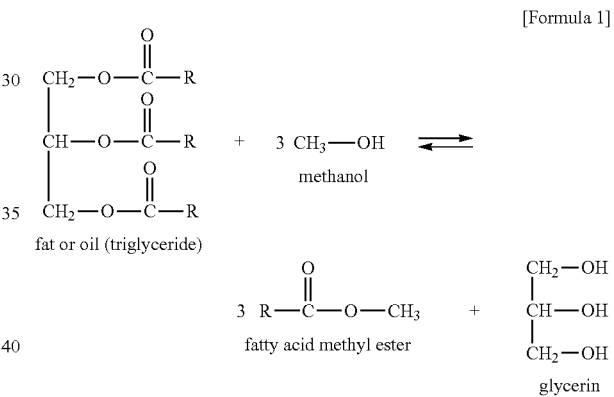

[Formula 1]

in the formula, R may be the same or different from each other and each represents an alkyl group containing 6 to 24 carbon atoms or an alkenyl group containing 6 to 24 carbon atoms and having one or more unsaturated bonds. More preferably, the alkyl group and the alkenyl group each contain 10 to 22 carbon atoms, and still more preferably contain 12 to 22 carbon atoms.

In the production method, due to use of the above-mentioned catalyst, the transesterification and esterification reactions can be simultaneously performed. Therefore, even if a fat or oil, which is a starting material, contains a free fatty acid, yield of a fatty acid alkyl ester can be improved without performing the esterification reaction step separately from the transesterification step, because the esterification reaction of the free fatty acid proceeds simultaneously in the transesterification step. In the above production method, glycerin is produced together with a fatty acid alkyl ester in the transesterification reaction, as shown by the above formula. In the present invention, purified glycerin can be easily produced industrially, and such glycerin is useful as a chemical raw material in various applications.

The fat or oil used in the above-mentioned contacting step contains a fatty acid ester of glycerin and may be any species capable of serving as a starting material for a fatty acid alkyl ester and/or glycerin, together with an alcohol. Thus, those generally called "fats and oils" may be used. It is generally preferred that fats and oils containing triglycerides (triesters of higher fatty acids with glycerin) as a main component and containing small amounts of diglycerides, monoglycerides and other minor components are used. Triolein, tripalmitin, and the like may be used.

Usable as the above-mentioned fats and oils are vegetable fats and oils such as rapeseed oil, sesame oil, soybean oil, corn oil, sunflower oil, palm oil, palm kernel oil, safflower oil, linseed oil, cottonseed oil, tung oil, castor oil, and coconut oil; animal fats and oils such as beef fat, lard, fish oil and whale oil; and various used edible fats and oils (waste cooking oil), among others. One or more species of them may be used. These fats and oils may contain organic acid, and may be subjected to a pretreatment such as deacidification and degumming.

If the above-mentioned fats and oils contain phospholipid, protein and the like as an impurity, it is preferable that the fats and oils are subjected to a degumming step by adding a mineral acid such as sulfuric acid, nitric acid, phosphoric acid or boric acid to the fats and oils in order to remove the impurity therefrom. According to the method for producing fatty acid alkyl esters and/or glycerin of the present invention, the catalyst is hardly inhibited by the mineral acid during the reaction. Therefore, fatty acid alkyl esters and/or glycerin can be produced efficiently, even if the fat or oil after the degumming step contains the mineral acid.

The alcohol used in the above-mentioned contacting step preferably has 1 to 6 carbon atoms and more preferably 1 to 3 carbon atoms, if a biodiesel fuel is produced. The alcohol containing 1 to 6 carbon atoms are, for example, methanol, ethanol, propanol, isopropyl alcohol, 1-butanol, 2-butanol, t-butyl alcohol, 1-pentanol, 3-pentanol, 1-hexanol, 2-hexanol. Methanol or ethanol is particularly preferable. These may be used singly or in combination of two or more species of them.

Polyol is preferable as the above alcohol if edible oil, a cosmetic, a medicine and the like is produced. Preferable examples of the above-mentioned polyol include ethylene glycol, propylene glycol, glycerin, pentaerythritol, and sorbitol. Among these, glycerin is preferable. These may be used singly or in combination of two or more species of them. Thus, if polyol is used as the above-mentioned alcohol, the method for producing fatty acid alkyl esters according to the present invention can be suitably employed for production of glycerides. In the above-mentioned method for producing fatty acid alkyl esters and/or glycerin, components other than the fat or oil, the alcohol, and the catalyst may exist.

The use amount of the above-mentioned alcohol is 1 to 30 times as large as the amount of theoretically needed alcohol in the reaction of the fat or oil with the alcohol. If the use amount is less than 1 time, the conversion rate might be insufficiently improved because the fat or oil might be insufficiently reacted with the alcohol. If the amount is more than 30 times, excess alcohol must be recovered or recycled, which possibly increases the costs. The use amount of the alcohol is more preferably 1.2 to 20 times, and still more preferably 1.5 to 15 times, and furthermore preferably 2 to 10 times.

The phrase "amount of theoretically needed alcohol" used herein means the number of moles of the alcohol corresponding to a saponification value of the fat or oil, and the amount can be calculated as follows:

[Amount of theoretically needed alcohol (kg)]=[(molecular weight of alcohol)]×[use amount of fat or oil (kg)×saponification value (g-KOH/kg-fat or oil)/56100].

If polyol is used as the above-mentioned alcohol, diglycerides are produced suitably by the production method of fatty acid alkyl esters according to the present invention. Such an embodiment is one of the preferable embodiments of the present invention. The diglycerides produced in such a manner can be suitably used in food fields, for example, as an additive for improving plasticity of a fat or oil. If the diglycerides are converted into edible fat or oil and mixed with various foods, it exhibits effects, such as prevention of obesity and inhibition of weight increase. Therefore, use of a diglyceride produced by the present invention as an edible fat or oil is also one of the preferable embodiments of the present invention.

In the above-mentioned embodiment in which diglycerides are produced, a reaction proceeds in a manner shown by the following formula if glycerin is used as the polyol, for example.

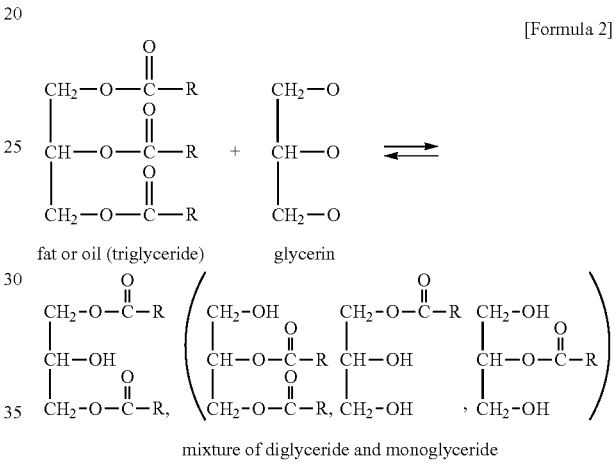

[Formula 2]

in the formula, R may be the same or different from each other and each represents an alkyl group containing 6 to 22 carbon atoms or an alkenyl group containing 6 to 22 carbon atoms and having one or more unsaturated bonds.

In the method for producing fatty acid alkyl esters and/or glycerin according to the present invention, the reaction temperature preferably has a lower limit of 100° C. and an upper limit of 300° C. If the reaction temperature is less than 100° C., the reaction rate might be insufficiently improved. If the reaction temperature is more than 300° C., suppression of a side reaction, such as alcohol decomposition, might be insufficient. More preferably, the lower limit is 120° C. and the upper limit is 270° C. Still more preferably, the lower limit is 150° C. and the upper limit is 235° C.

In the method for producing fatty acid alkyl esters and/or glycerin, the catalyst preferably contains an active component not eluting off at the reaction temperature within the above-mentioned range. Such a catalyst can maintain its activity even at a high reaction temperature, which allows the reaction to proceed well.

In the method for producing fatty acid alkyl esters and/or glycerin according to the present invention, the reaction pressure preferably has a lower limit of 0.1 MPa and an upper limit of 10 MPa. If the reaction pressure is less than 0.1 MPa, the reaction rate might be insufficiently improved. If the reaction pressure is more than 10 MPa, a side reaction might tend to proceed easily. In addition, a special apparatus which can endure high pressure is needed, and hence utility costs and equipment costs might not be reduced enough. More preferably, the lower limit of the reaction pressure is 0.2 MPa and the upper limit thereof is 9 MPa. Still more preferably, the lower limit of the reaction pressure is 0.3 Mpa and the upper limit thereof is 8 MPa.

The reaction can proceed well because, as mentioned above, the catalyst with high activity is used in the method for producing fatty acid alkyl esters and/or glycerin of the present invention, even under the above-mentioned conditions of the reaction temperature and pressure.

The above-mentioned catalyst (catalyst including the manganese element and the trivalent metal element) can be used under supercritical condition of an alcohol to be used. The "supercritical condition" means that a range over the specific critical temperature and the critical pressure of a substance itself. If methanol is used as the alcohol, the state means a temperature of 239° C. or more and a pressure of 8.0 MPa or more. Use of the catalyst permits efficient production of fatty acid alkyl esters and/or glycerin even under the supercritical state.

In the method for producing fatty acid alkyl esters and/or glycerin, the catalyst amount used in the reaction preferably has a lower limit of 0.5% by weight and an upper limit of 20% by weight, relative to the total fed amount of the fat or oil, the alcohol and the catalyst, for example, in a batch system. If the lower limit is less than 0.5% by weight, the reaction rate might be insufficiently improved. If the upper limit is more than 20% by weight, catalyst costs might not be reduced enough. The lower limit is more preferably 1.5% by weight, and the upper limit is more preferably 10% by weight. In a fixed bed flow system, liquid hourly space velocity (LHSV) calculated by the following formula preferably has a lower limit of 0.1 $hr^{-1}$ and an upper limit of 5 $hr^{-1}$. More preferably, the lower limit is 0.2 $hr^{-1}$ and the upper limit is 3 $hr^{-1}$.

LHSV ($hr^{-1}$)={flow volume of a fat or oil per hour ($L \cdot hr^{-1}$)+flow amount of an alcohol per hour ($L \cdot hr^{-1}$)}/volume of a catalyst ($L$)

In the production method of the present invention, the reaction liquid after completion of the reaction may contain an unreacted starting material, an intermediate glyceride and the like because use of the catalyst permits an easy recycle process. In this case, it is preferable to recover the unreacted glyceride and the free fatty acid (FFA), and to reuse the recovered glyceride and free fatty acid as a starting material for the reaction in the second and subsequent stages. The recovery of such unreacted glyceride and free fatty acid can be carried out, for example, by removing low-boiling components, such as alcohol and water from the mixture after the reaction in the absence of the catalyst, and then separating the ester phase including the unreacted glyceride and the free fatty acids from glycerol phase by phase separation. This procedure makes it possible to produce a high-purity fatty acid alkyl ester and glycerin with high yield and to reduce purification costs more sufficiently.

The fatty acid alkyl esters produced by the method according to the present invention are used suitably for various uses, for example, as an industrial raw material, a raw material for pharmaceuticals, a fuel and the like. Among these, diesel fuel containing fatty acid alkyl esters made from vegetable fats and oils or waste cooking oil, produced by the above-mentioned production method, can sufficiently reduce utility costs and equipment costs in the production step. Furthermore, the diesel fuel can sufficiently contribute to environmental preservation from the production stages because the production method needs no catalyst-recovering step and the catalyst can be used repeatedly. Therefore, such a biodiesel fuel can be preferably used as various fuels. Such a diesel fuel containing the fatty acid alkyl ester produced by the above production method is also one of the embodiments of the present invention.

FIGS. 1 and 2 are views showing a preferable embodiment of the production steps in the method for producing fatty acid alkyl esters and/or glycerin according to the present invention. The present invention is not limited to these embodiments. FIG. 1 shows a step of bringing a fat or oil into contact with an alcohol by a batch system in the presence of a catalyst. In such an embodiment, the fat or oil and the alcohol are mixed with the catalyst, and subjected to reaction. This reaction liquid is subjected to filtration and the like, thereby separating and removing a sold catalyst from a liquid phase. Then, the alcohol is removed by evaporation. This reaction liquid is kept standing and separated into an ester phase mainly containing a fatty acid alkyl ester and glycerides and a glycerin phase mainly containing glycerin and alcohol. Then, the alcohol and the catalyst are added to the ester phase separated from the glycerin phase to cause further reaction, and the obtained mixture is separated into an ester phase and a glycerin phase. Finally, a fatty acid alkyl ester and glycerin are obtained. Thus-produced fatty acid alkyl ester and/or glycerin may be further purified by distillation and the like depending on purpose.

FIG. 2 shows a step of bringing a fat or oil, and an alcohol into contact with a solid catalyst, which is a stationary phase and filled in a reactor of a fixed bed continuous flow reactor. The mixture reacted in the reactor filled with the catalyst is kept standing in a settler to separate into an ester phase and a glycerin phase. In this case, it is preferable that the alcohol is removed by evaporation before the reacted liquid is kept standing in the settler because the ester phase and the glycerin phase are separated with higher efficiency. The ester phase separated from the glycerin phase is further reacted with an alcohol in the reactor filled with the catalyst to produce a reaction liquid. Then, the alcohol is removed by evaporation from this reaction liquid, and the residual reaction liquid is kept standing in the settler to separate into an ester phase and a glycerin phase. Thus-produced fatty acid alkyl ester and/or glycerin may be further purified by distillation and the like, depending on purpose.

According to the method for producing fatty acid alkyl esters and/or glycerin of the present invention, the step of bringing the catalyst into contact with the reaction liquid may be performed by a batch system or a continuous flow system. According to the batch system, it is preferable that the catalyst is charged into a mixture of the fat or oil with the alcohol.

It is preferable that the contacting step is performed by a fixed bed flow system because the step for catalyst separation is not necessary according to the method for producing fatty acid alkyl esters and/or glycerin of the present invention. That is, it is preferable that the contacting step is performed with a fixed bed flow reactor. If the catalyst is brought into contact with the starting materials for the reaction inside the reactor equipped with a stationary phase of the solid catalyst, a yield of the reaction can be increased in comparison to the case that the reaction is performed by a batch system. Further, no leaching (elution) of the catalyst occurs even if the catalyst is repeatedly used in the reaction, and the catalyst can be used for a long period of time. As a result, the life of the catalyst lengthens.

The present invention is also a catalyst for producing fatty acid alkyl esters and/or glycerin, used in the above-mentioned method for producing fatty acid alkyl esters and/or glycerin.

As a configuration, structure, production method, specific example and the like of the above-mentioned catalyst, those mentioned above are preferred. If such a catalyst is used in the above-mentioned production method, particularly preferably in the production method using a reactor equipped with a stationary phase of the solid catalyst, no leaching (elution) occurs even if the catalyst is repeatedly used in the reaction, and the catalyst can be used for a long period of time. Use of the catalyst in the production method using a reactor equipped with a stationary phase of the solid catalyst can simplify the separation and removal step of the catalyst, which is economically excellent. The production method of the present invention may include other steps such as a separation step and a purification step, as mentioned above.

Further, a method of using the above-mentioned oxide as a catalyst in the method for producing fatty acid alkyl esters and/or glycerin comprising a step of bringing a fat or oil into contact with an alcohol in the presence of a catalyst is also one of the present invention.

The details of the above-mentioned use method are the same as in the above-mentioned production method.

EFFECT OF THE INVENTION

The method for producing fatty acid alkyl esters and/or glycerin according to the present invention has the above-mentioned configuration. Therefore, the method has the following operation and effects.

In view of simplification of the reaction processes,
(1) the step of separating and removing the catalyst can be simplified or omitted;
(2) neither the step of neutralizing and removing free fatty acid nor the esterification step using an acid catalyst is needed;
(3) no saponification of free fatty acid occurs; and
(4) not only the transesterification of the fat or oil but also the esterification of the free fatty acid in the fat or oil simultaneously proceed.

In view of simplification of the purification processes, that is, easier production of purified glycerin,
(1) the alcohol can be sufficiently removed by evaporation and the distribution equilibrium of liquid-liquid two phases can be improved (mutual solubility decreases) because no catalytic reverse reaction is generated. Hence, the product can be separated well; and
(2) the fatty acid alkyl ester can be produced with high selectivity, because the alcohol is hardly decomposed (dehydration or coking) due to the absence of a strong acid point or base point on the catalyst surface; and the catalyst is hardly affected by a small amount of the metal components contained in the fat or oil, or the mineral acid used for the pretreatment.

BRIEF DESCRIPTION OF DRAWINGS

FIG. 3-1 is a chart showing an XRD pattern of a catalyst prepared in Catalyst Preparation Example 1.

FIG. 3-2 is a chart showing an XRD pattern of a catalyst prepared in Catalyst Preparation Example 2.

FIG. 3-3 is a chart showing an XRD pattern of a catalyst prepared in Catalyst Preparation Example 3.

FIG. 3-4 is a chart showing an XRD pattern of a catalyst prepared in Catalyst Preparation Example 4.

FIG. 3-5 is a chart showing an XRD pattern of a catalyst prepared in Catalyst Preparation Example 5.

FIG. 3-6 is a chart showing an XRD pattern of a catalyst prepared in Catalyst Preparation Example 6.

FIG. 3-7 is a chart showing an XRD pattern of a catalyst prepared in Catalyst Preparation Example 7.

FIG. 4 is a chart showing an XRD pattern of a catalyst prepared in Catalyst Preparation Reference Example 1.

FIG. 5 is a chart showing a variation in a conversion rate of palm oil, a yield of methyl ester, and a yield of glycerin in Example 1.

FIG. 6 is a chart showing a variation in a conversion rate of palm oil, a yield of methyl ester, and a yield of glycerin in Example 2.

FIG. 7 is a chart showing a variation in a conversion rate of palm oil, a yield of methyl ester, and a yield of glycerin in Example 3.

EXPLANATION OF NUMERAL(S) AND SYMBOL(S)

1-*a*: fat or oil, alcohol and catalyst
1-*b*: glycerin phase (glycerin)
1-*c*: the first separation
1-*d*: evaporation of alcohol
1-*e*: ester phase (fatty acid alkyl ester, glycerides)
1-*f*: alcohol, catalyst
1-*g*: the second separation
1-*h*: ester phase (fatty acid alkyl ester)
1-*i*: glycerin phase (glycerin)
1-*j*: evaporation of alcohol
2-*a*: fat or oil, alcohol
2-*b*: catalyst
2-*c*: glycerin phase (glycerin)
2-*d*: settler
2-*e*: evaporation of alcohol
2-*f*: ester phase (fatty acid alkyl ester, glycerides)
2-*g*: alcohol
2-*h*: catalyst
2-*i*: settler
2-*j*: ester phase (fatty acid alkyl ester)
2-*k*: glycerin phase (glycerin)
2-*m*: evaporation of alcohol
3-1*a*: peak of $Mn_2O_3$
3-2*a*: peak of $Mn_2O_3$
3-3*a*: peak of $Al_2O_3$
3-4-*a*: peak of $Mn_2AlO_4$ 3-4-b: peak of $MnAl_2O_4$
4a: peak of $[Mn_{0.67}Al_{0.33\ (OH)2}][(NO_3)_{0.33}\cdot yH_2O]$

BEST MODES FOR CARRYING OUT THE INVENTION

The present invention is mentioned in more detail below with reference to Examples, but the present invention is not limited to only these Examples. The term "%" represents "% by weight" unless otherwise specified.

Conversion rates and yields in Examples were calculated according to the following formula.

Conversion rate (mol %)=Number of moles of consumed fat or oil or fatty acid on completion of reaction/Number of moles of fed fat or oil or fatty acid×100

Yield of methyl ester (mol %)=Number of moles of produced methyl ester on completion of reaction/Number of moles of fed effective fatty acid×100

Yield of glycerin (mol %)=Number of moles of produced free glycerin on completion of reaction/Number of moles of fed effective glycerin component×100

The "effective fatty acid" means a triglyceride, a diglyceride, and a monoglyceride, a free fatty acid of fatty acid contained in the fat or oil. That is, the number of moles of a fed (additional) effective fatty acid is calculated by the following formula.

Number of moles of fed effective fatty acid=[amount of fed fat or oil (g)×saponification value of fat or oil (mg-KOH/g-fat or oil)/56100]+number of moles of fed fatty acid The term "effective glycerin component" means a component capable of producing glycerin by the method of the present invention, and specifically, a triglyceride, a diglyceride, and a monoglyceride of fatty acid contained in the fat or oil. The content of the effective glycerin component can be determined by gas chromatography of free glycerin produced by saponification of the fat or oil (starting material for the reaction).

CATALYST PREPARATION EXAMPLE 1

Aluminum oxide 100 g produced by SIGMA-ALDRICH Corp. (trade name: Aluminum Oxide, activated, basic, ~150 mesh) was impregnated with a 50% aqueous solution of manganese nitrate 120 g and the aqueous solution of manganese nitrate was supported on the aluminum oxide. This mixture was dried at 100° C. one day and night and then calcined under air flow at 800° C. for 5 hours.

Figure 1:
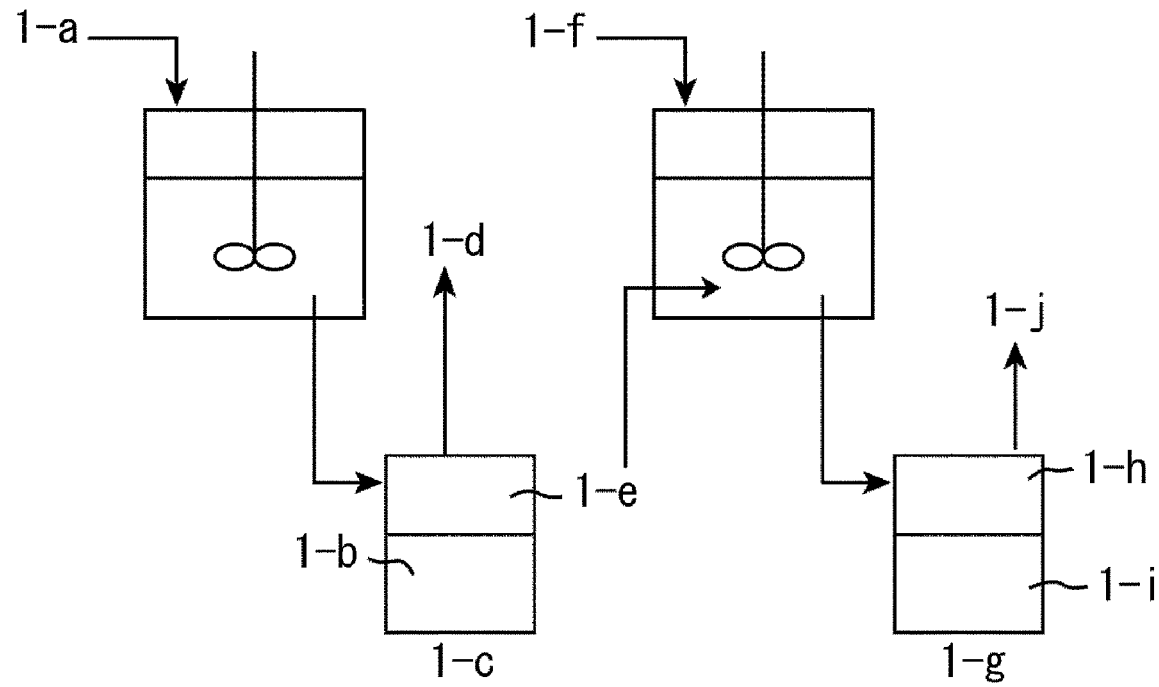
FIG. 1 is a schematic view showing one of the preferable embodiments of production steps in the method for producing fatty acid alkyl esters and/or glycerin according to the present invention.
Figures 1, 3:
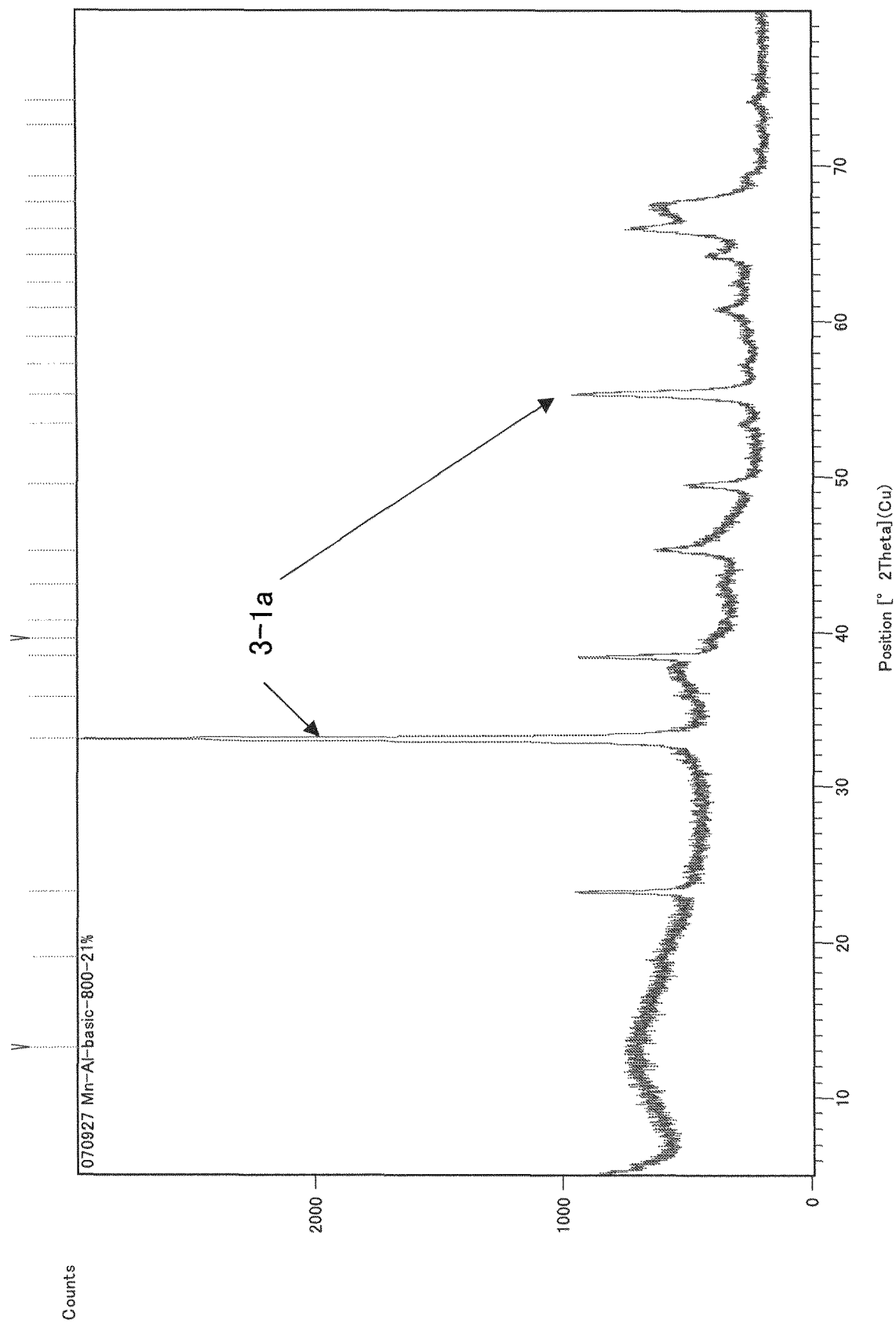
Figures 2, 3:
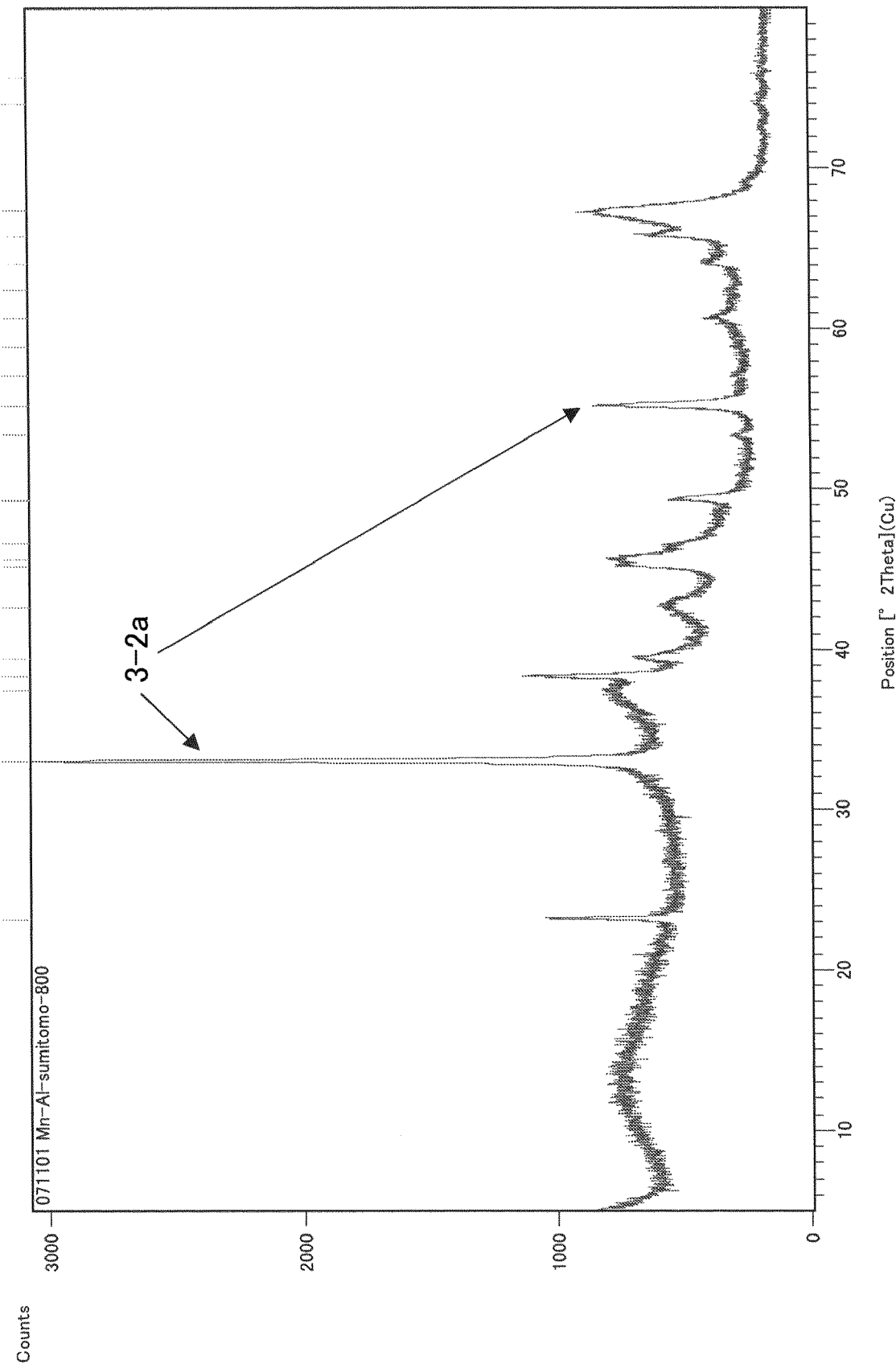
Figure 3:
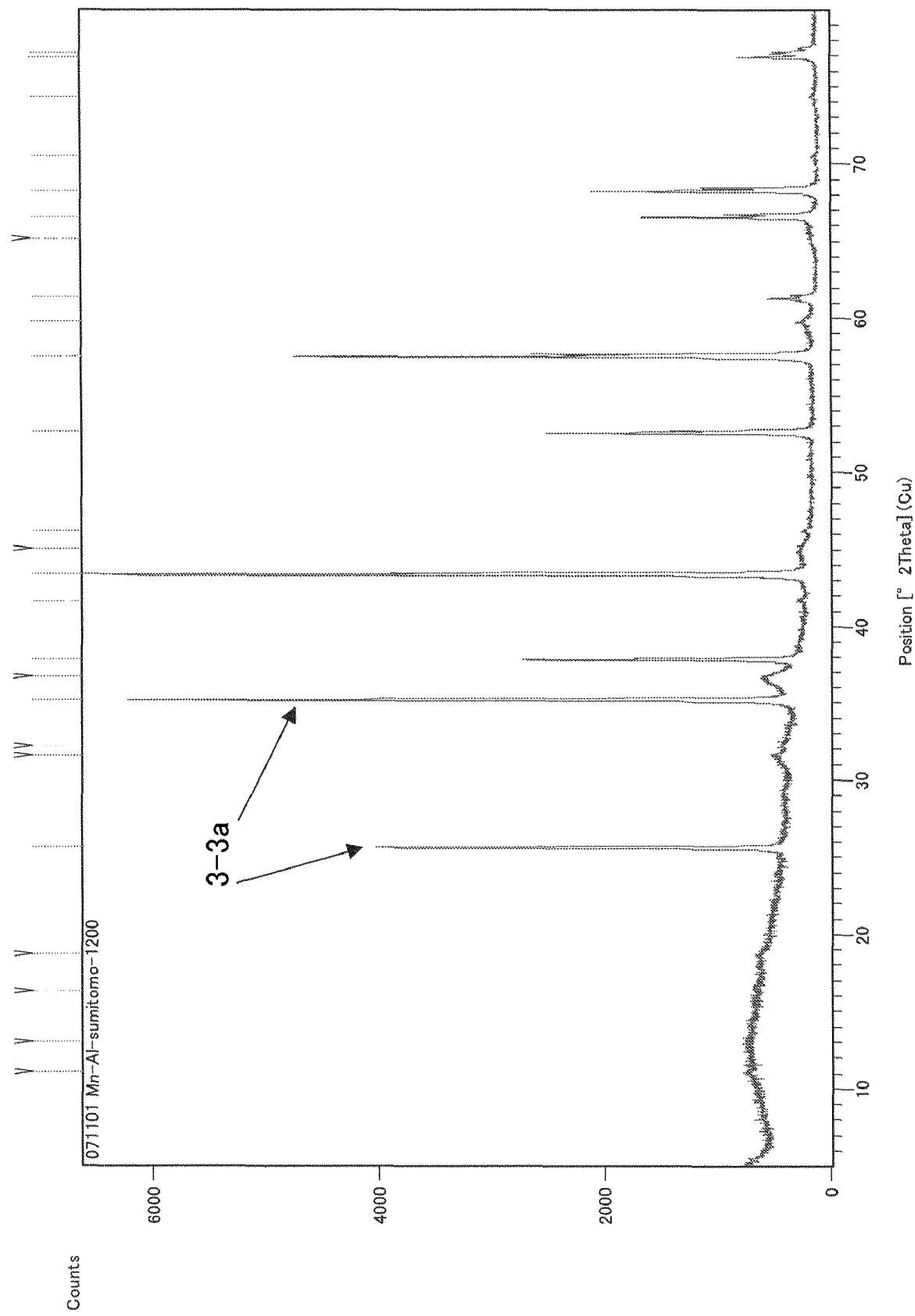

XRD measurement showed that the catalyst obtained after the calcination included $Mn_2O_3$. FIG. 3-1 shows an XRD pattern of the catalyst obtained in Catalyst Preparation Example 1. This catalyst was subjected to X-rays fluorescence analysis (XRF), which showed that the catalyst included 23% as $Mn_2O_3$ and 77% as $Al_2O_3$.

CATALYST PREPARATION EXAMPLE 2

Activated alumina AC-12 produced by Sumitomo Chemical Co., Ltd., 73.6 g was impregnated with a 50% aqueous solution of manganese nitrate 36.2 g and the aqueous solution of manganese nitrate was supported on the activated alumina AC-12. This mixture was dried on an evaporating dish on a hot-water bath and then dried in a dryer at 120° C. one day and night and then calcined under air flow at 800° C. for 5 hours.

Figure 2:
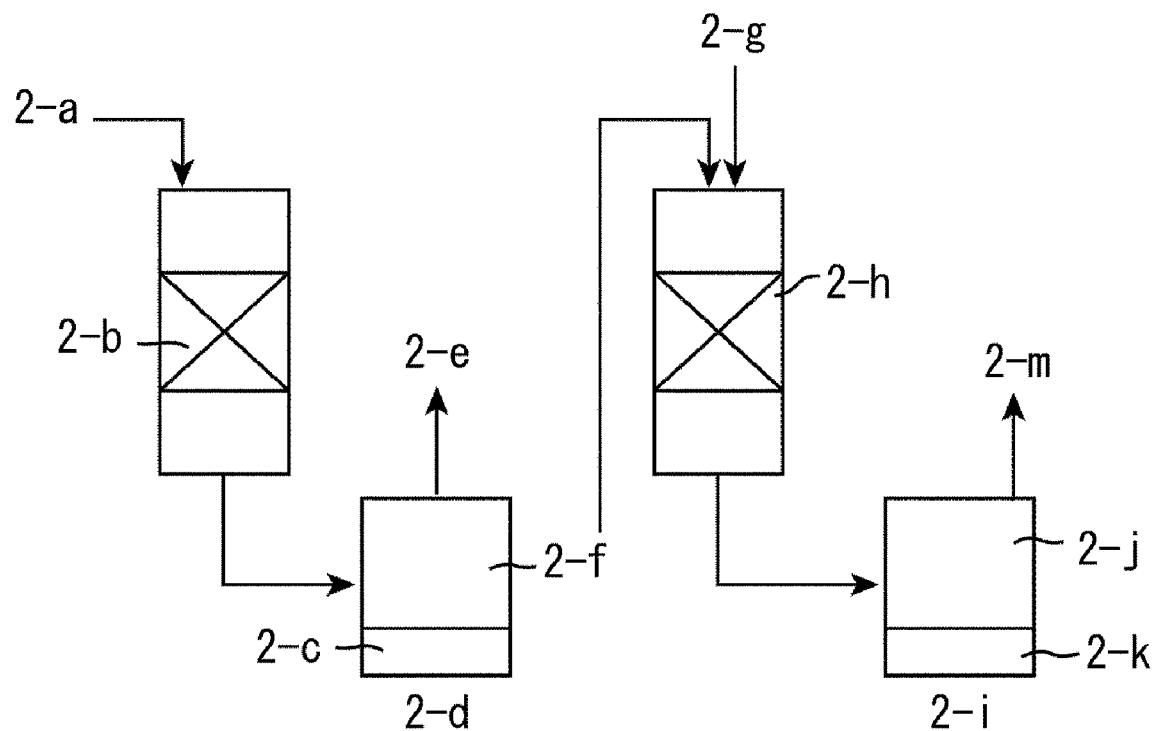
FIG. 2 is a schematic view showing one of the preferable embodiments of production steps in the method for producing fatty acid alkyl esters and/or glycerin according to the present invention.

XRD measurement showed that the catalyst obtained after the calcination included $Mn_2O_3$. FIG. 3-2 shows an XRD pattern of the catalyst obtained in Catalyst Preparation Example 2. This catalyst was subjected to X-rays fluorescence analysis (XRF), which showed that the catalyst included 10% as $Mn_2O_3$ and 90% as $Al_2O_3$.

CATALYST PREPARATION EXAMPLE 3

A catalyst was prepared in the same manner as in Catalyst Preparation Example 2, except that the calcination temperature was 1200° C. XRD measurement showed that the catalyst obtained after the calcination included $Al_2O_3$. FIG. 3-3 shows an XRD pattern of the catalyst obtained in Catalyst Preparation Example 3. This catalyst was subjected to X-rays fluorescence analysis (XRF), which showed that the catalyst included 10% as $Mn_2O_3$ and 90% as $Al_2O_3$.

CATALYST PREPARATION EXAMPLE 4

Manganese carbonate produced by Wako Pure Chemical Industries, Ltd., 12.8 g was mixed well with aluminum hydroxide produced by Wako Pure Chemical Industries, Ltd., 3.9 g. The mixture was calcined at 1500° C. for 6 hours to give a catalyst.

Figures 3, 4:
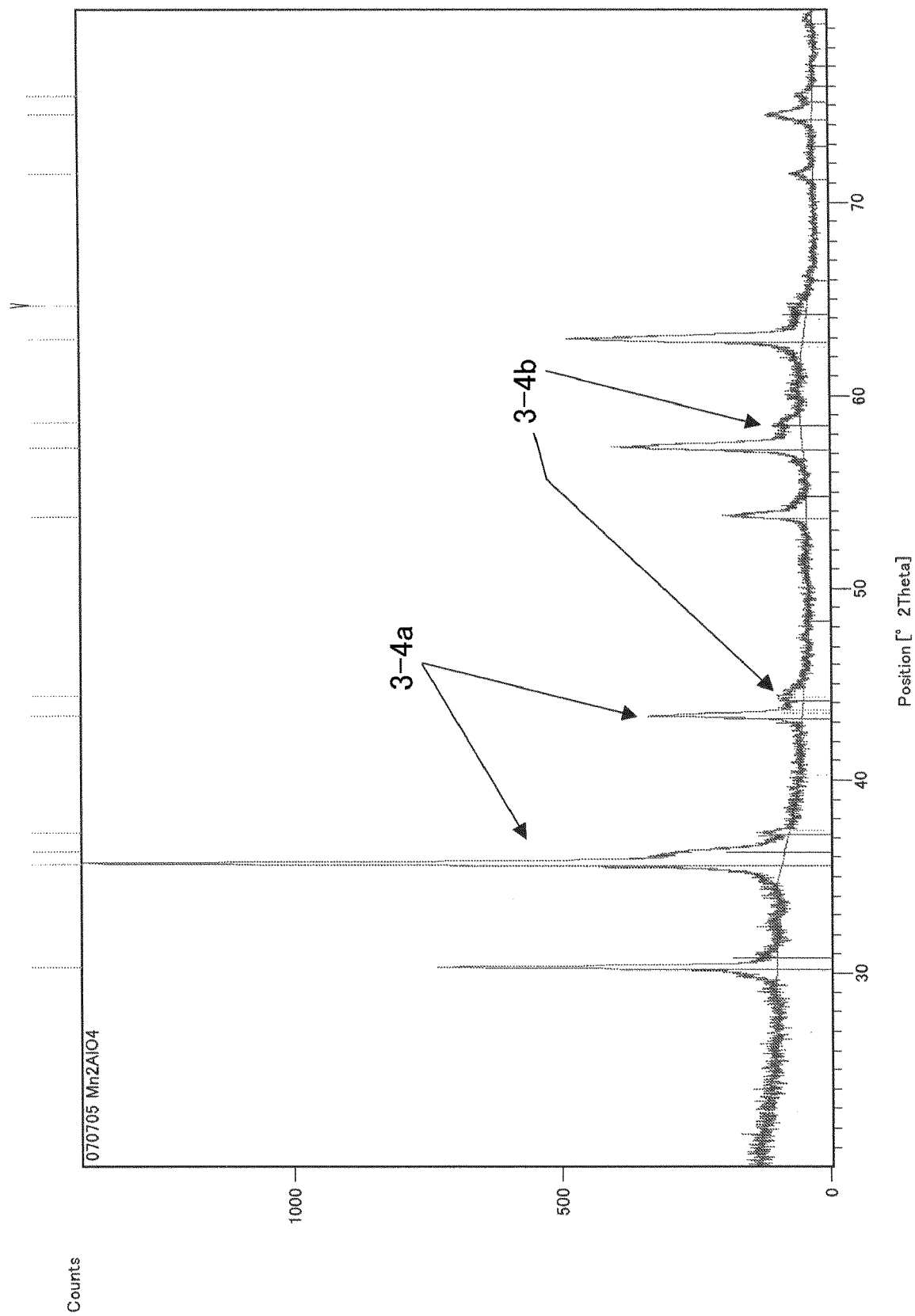

XRD measurement showed that the catalyst obtained after the calcination included $Mn_2AlO_4$ and $MnAl_2O_4$. FIG. 3-4 shows an XRD pattern of the catalyst obtained in Catalyst Preparation Example 4.

CATALYST PREPARATION EXAMPLE 5

Activated alumina AC-12 produced by Sumitomo Chemical Co., Ltd., 40.0 g was impregnated with a solution which had been previously prepared by mixing a 50% aqueous solution of manganese nitrate 18.3 g with zirconium nitrate produced by DAIICHI KIGENSO KAGAKU KOGYO CO., LTD. (trade name: Zircosol ZN, including 25% of $ZrO_2$) 5.7 g. This mixture was dried on an evaporating dish on a hot-water bath and then dried in a dryer at 120° C. one day and night and then calcined under air flow at 800° C. for 5 hours.

Figures 3, 4, 5:
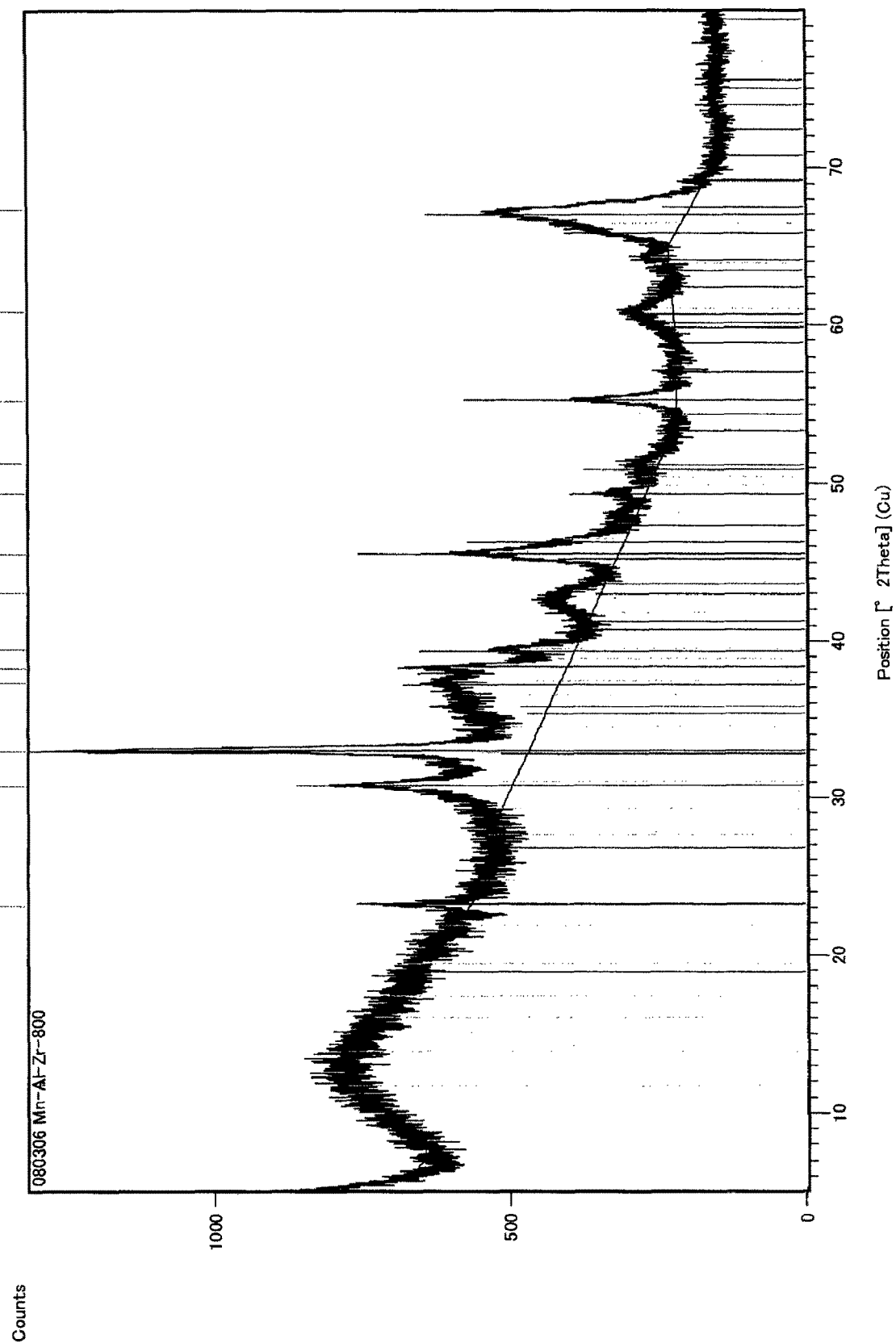

XRD measurement showed that the catalyst obtained after the calcination included $Mn_2O_3$, $ZrO_2$, and $Al_2O_3$. FIG. 3-5 shows an XRD pattern of the catalyst obtained in Catalyst Preparation Example 5 X-rays fluorescence analysis (XRF) of this catalyst showed that the catalyst included 19.0% as $Mn_2O_3$ and 1.8% as $ZrO_2$, and 79.2% as $Al_2O_3$.

CATALYST PREPARATION EXAMPLE 6

Silica alumina powder 28.2 g, obtained by pulverizing and classifying a silica alumina product, 50% of which was composed of $Al_2O_3$, into 125 to 500 μm, was impregnated with a 50% aqueous solution of manganese nitrate 12.9 g and the aqueous solution of manganese nitrate was supported on the silica alumina powder. This mixture was dried on an evaporating dish on a hot-water bath and then dried in a dryer at 120° C. one day and night and then calcined under air flow at 800° C. for 5 hours. XRD measurement showed that the catalyst obtained after the calcination included $Mn_2O_3$. FIG. 3-6 shows an XRD pattern of the catalyst obtained in Catalyst Preparation Example 6.

CATALYST PREPARATION EXAMPLE 7

A catalyst was prepared in the same manner as in Catalyst Preparation Example 2, except that the calcination temperature was 600° C.

FIG. 3-7 shows an XRD pattern of the catalyst obtained in Catalyst Preparation Example 7. This catalyst was subjected to X-rays fluorescence analysis (XRF), which showed that the catalyst included 10% as $Mn_2O_3$ and 90% as $Al_2O_3$.

CATALYST PREPARATION REFERENCE EXAMPLE 1

Purified water was added to a 50.2% aqueous solution of manganese nitrate 35.7 g and aluminum nitrate nonahydrate 18.8 g to give a mixture 100 mL. To this mixture, an aqueous solution of 1 mol/L sodium carbonate 50 mL was added dropwise while a pH of the mixture was adjusted to 9 with an aqueous solution of 1 mol/L sodium hydroxide. This mixture was stirred at 40° C. for one hour. A solid was filtrated from the mixture, and the obtained solid was rinsed and dried. XRD measurement showed that the catalyst obtained after the drying had a structure of $[Mn_{0.67}Al_{0.33}(OH)_2][(NO_3)_{0.33} \cdot yH_2O]$. FIG. 4-1 shows an XRD pattern of the catalyst obtained in Catalyst Preparation Reference Example 1.

CATALYST PREPARATION COMPARATIVE EXAMPLE 1

Manganese (II) phosphate (monobasic) (tetrahydrate) produced by SAN'EI KAKO Co., LTD., 50 g was calcined at 600° C. for 5 hours under air atmosphere, and then molded at a pressure of 20 t for 3 minutes with a press-molding machine (product of Maekawa Testing Machine MFG Co., LTD.). Then, the molded sample was pulverized and shifted to give particles with 250 μm to 850 μm.

EXAMPLE 1

Reaction conditions:
Reaction temperature: 200° C.
Reaction pressure: 5 MPa
Catalyst: Mn—Al (prepared in the above-mentioned Catalyst Preparation Example 1)
Catalyst amount: 15 mL, LHSV=1 $hr^{-1}$,
Reaction starting material: purified palm oil 6.3 $g \cdot hr^{-1}$ and methanol 6.3 $g \cdot hr^{-1}$, the methanol in an amount equal to 9 times the theoretically needed amount was supplied relative to palm oil.

The reaction liquid was sampled after 110 hours, 234 hours, 326 hours, and 452 hours since the start of the reaction. As a result, no reduction was observed in a conversion rate of the palm oil, a yield of methyl ester, and a yield of glycerin even after 450 hours from the start of the reaction. FIG. 5 is a chart showing a variation in a conversion rate of palm oil, a yield of methyl ester, and a yield of glycerin in Example 1.

EXAMPLE 2

Reaction conditions:
Reaction temperature: 200° C.,
Reaction pressure: 5 MPa,
Catalyst: Mn—Al (prepared in the above-mentioned Catalyst Preparation Example 1)
Catalyst amount: 15 mL, LHSV=1 $hr^{-1}$,
Reaction starting material: purified palm oil 6.3 $g \cdot hr^{-1}$ and methanol 6.3 $g \cdot hr^{-1}$, the methanol in an amount equal to 9 times the theoretically needed amount was supplied relative to palm oil.

After the reaction was stabilized, moisture was added to the starting materials until the reaction system contained 1500 ppm of moisture. The reaction liquid was sampled after 114 hours, 206 hours, and 332 hours since the start of the reaction.

Figures 3, 4, 5, 6:
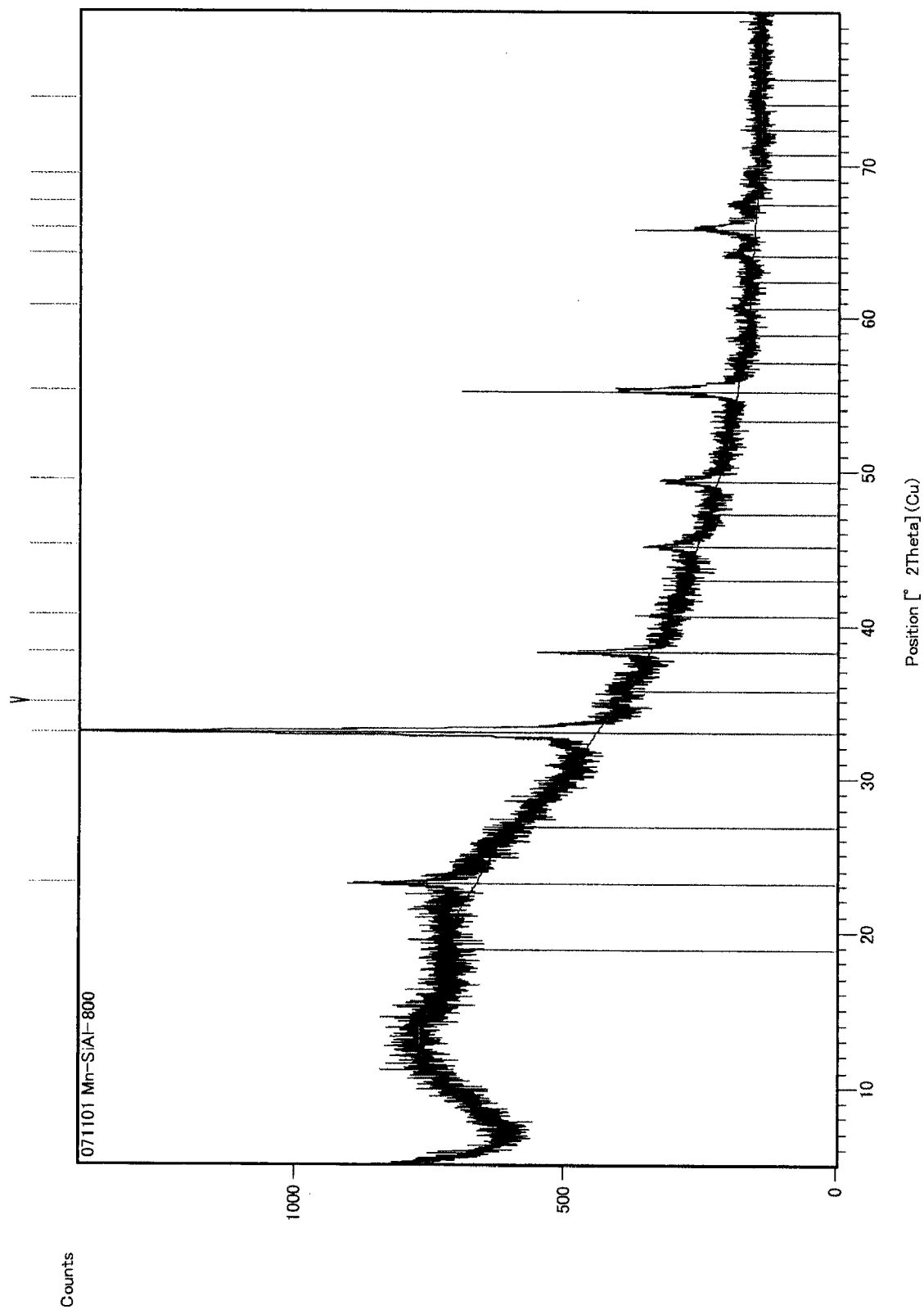

As a result, no reduction was observed in a conversion rate of the palm oil, a yield of methyl ester, and a yield of glycerin even after 300 hours from the addition of moisture. FIG. 6 is a chart showing a variation in a conversion rate of palm oil, a yield of methyl ester, and a yield of glycerin in Example 2.

EXAMPLE 3

Figures 3, 4, 5, 6, 7:
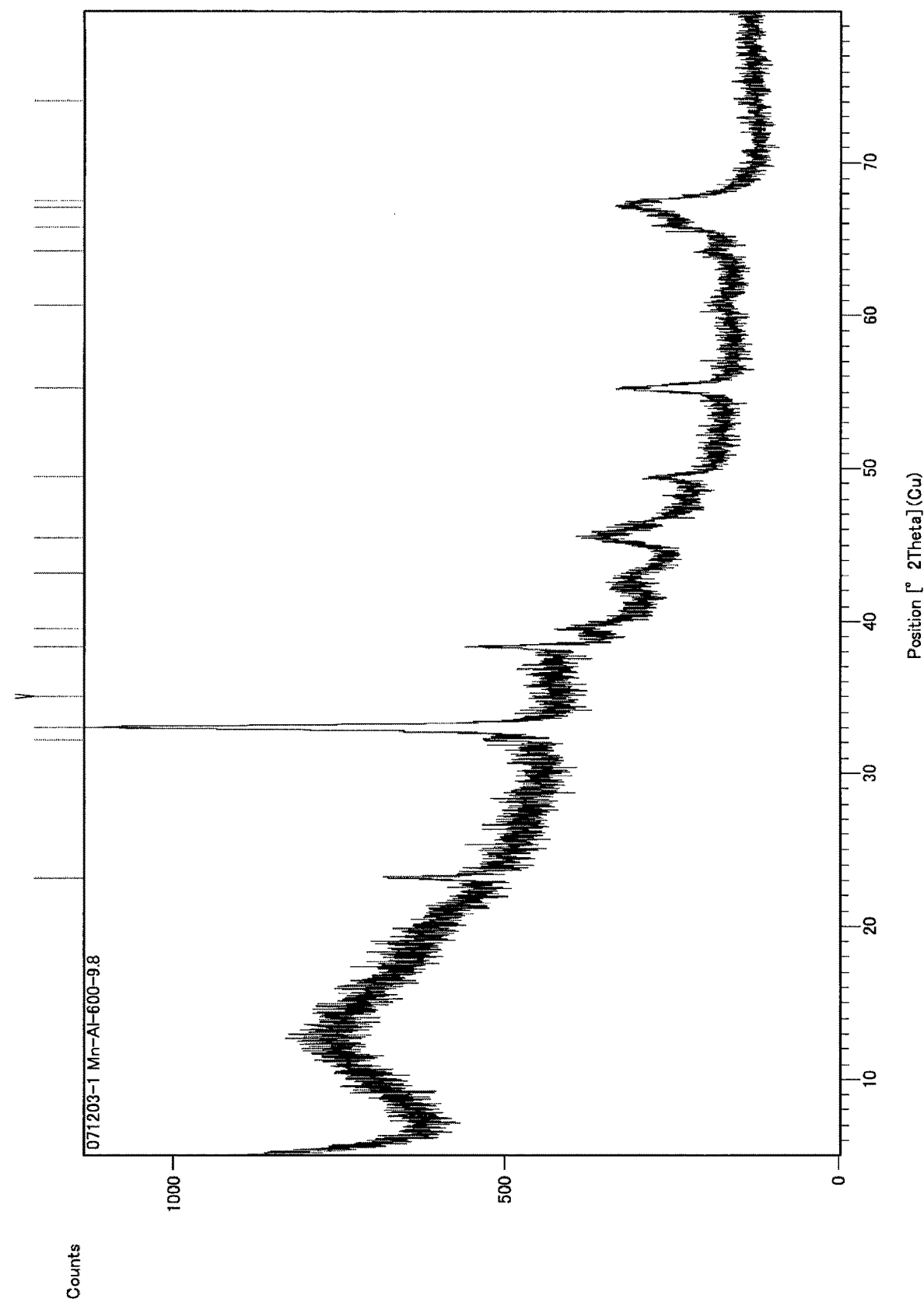
Figure 4:
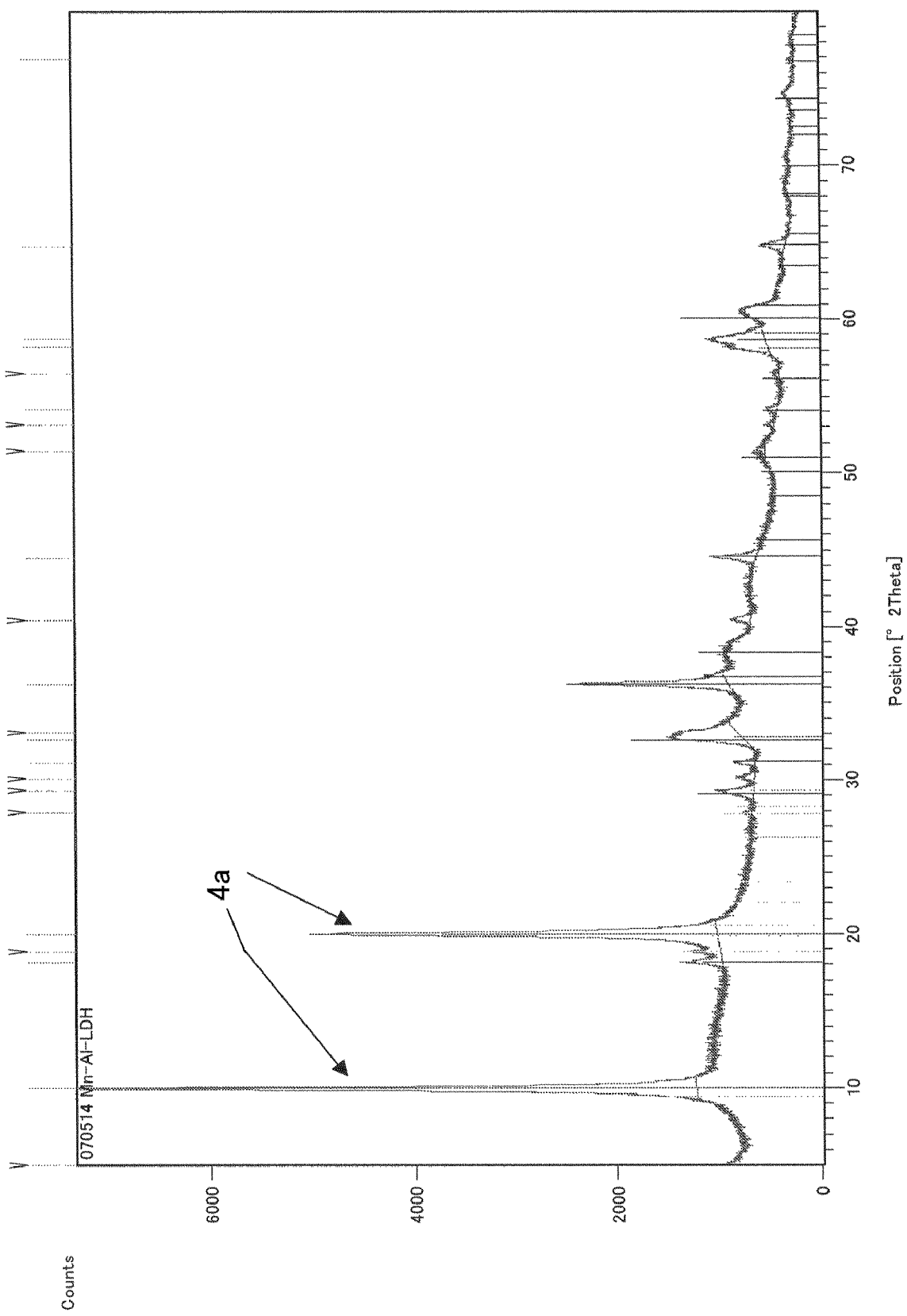
Figure 5:
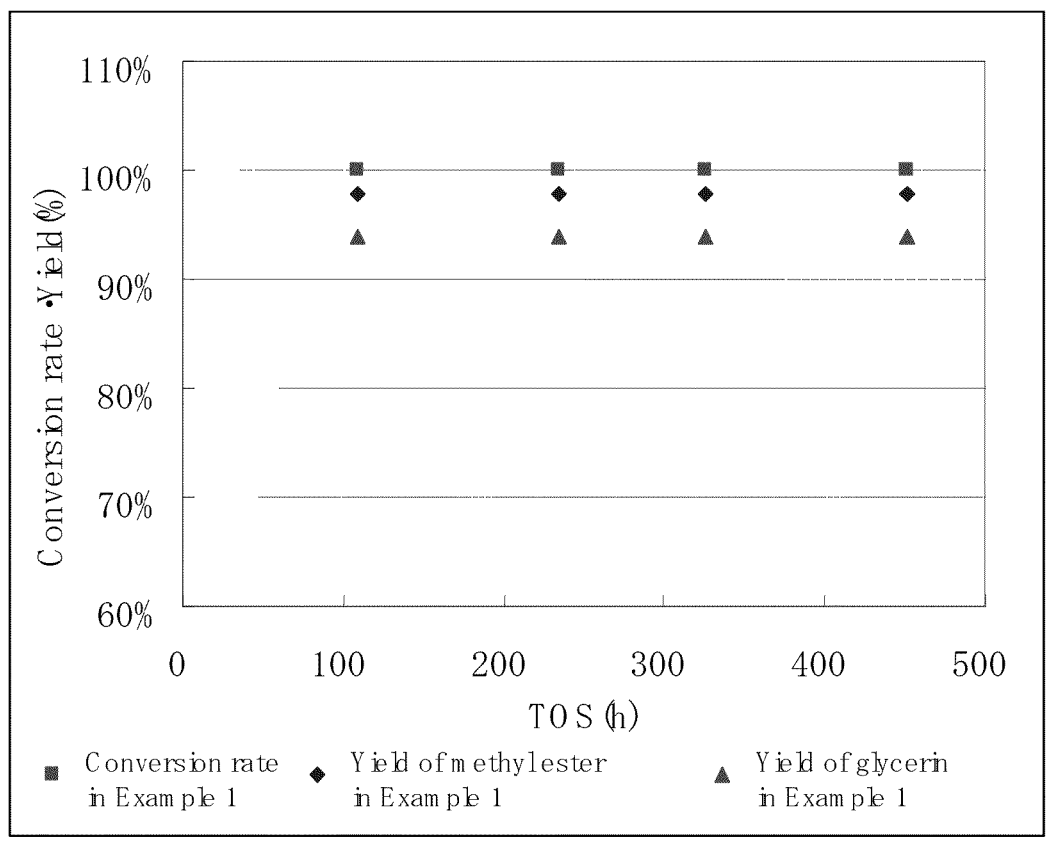
Figure 6:
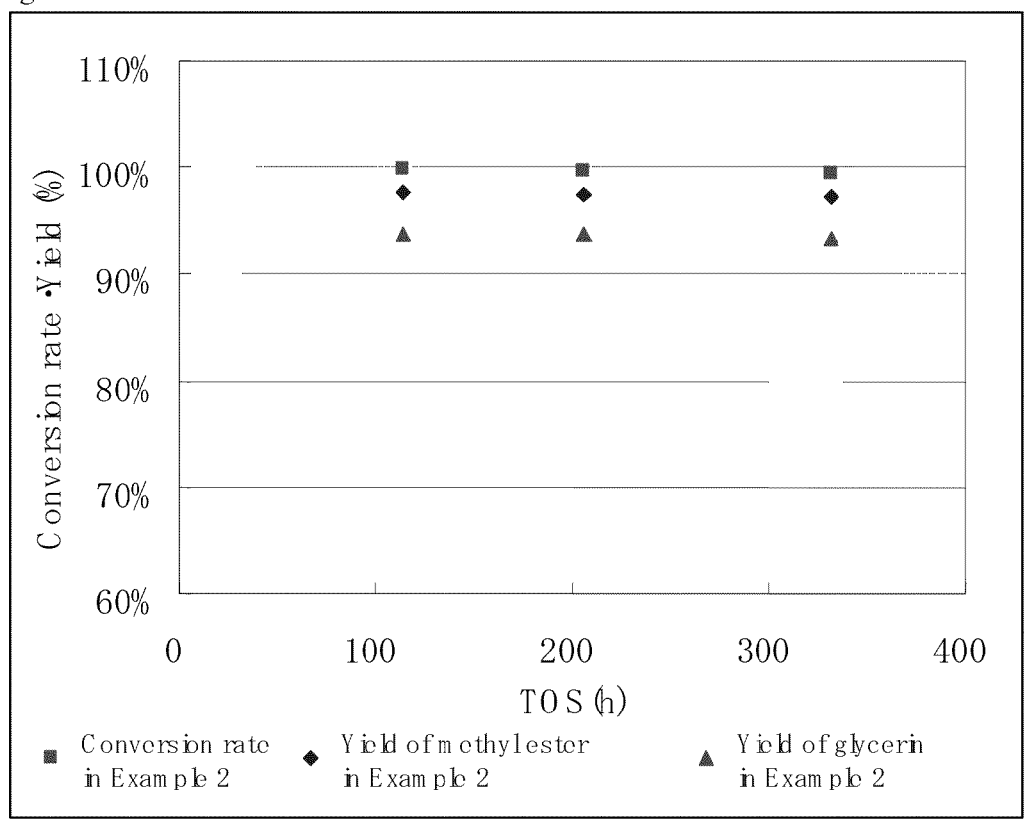
Figure 7:
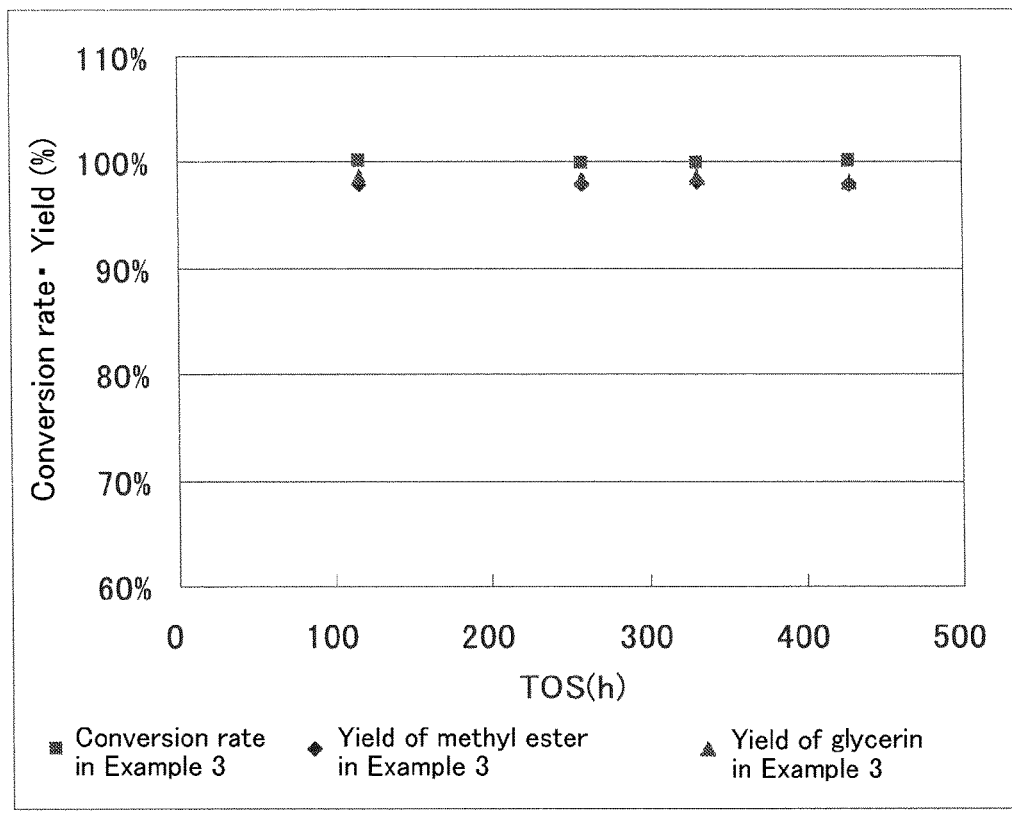

The reaction was performed in the same manner as in Example 1, except that the catalyst which had been prepared in Catalyst Preparation Example 2 was used. The reaction liquid was sampled after 116 hours, 258 hours, 332 hours, and 428 hours since the start of the reaction. As a result, no reduction was observed in a conversion rate of the palm oil, a yield of methyl ester, and a yield of glycerin even after 400 hours from the start of the reaction. FIG. 7 is a chart showing a variation in a conversion rate of palm oil, a yield of methyl ester, and a yield of glycerin in Example 3.

EXAMPLE 4

Figure 8:
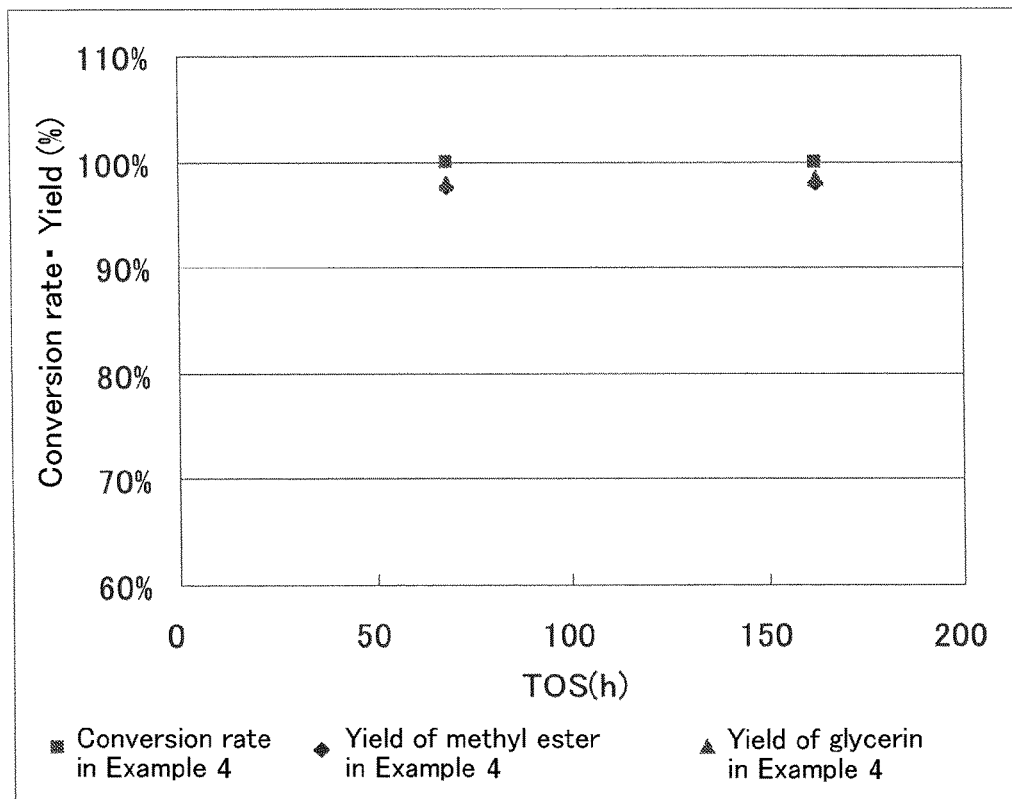
FIG. 8 is a chart showing a variation in a conversion rate of palm oil, a yield of methyl ester, and a yield of glycerin in Example 4.

The reaction was performed in the same manner as in Example 1, except that the catalyst which had been prepared in Catalyst Preparation Example 3 was used. The reaction liquid was sampled after 68 hours and 162 hours since the start of the reaction. As a result, no reduction was observed in a conversion rate of the palm oil, a yield of methyl ester, and a yield of glycerin even after 150 hours from the start of the reaction. FIG. 8 is a chart showing a variation in a conversion rate of palm oil, a yield of methyl ester, and a yield of glycerin in Example 4.

EXAMPLE 5

The following reaction was performed using the catalyst which had been prepared in Catalyst Preparation Example 4 as a catalyst. Palm oil 61.5 g, methanol 20 g, and the catalyst 2.5 g which had been prepared in Catalyst Preparation Example 4 were charged into a 200 mL autoclave. After nitrogen substitution, the reaction was allowed to proceed at a reaction temperature of 200° C. for 24 hours under internal stirring. The conversion rate of the palm oil was 88 mol %. The leaching amounts of the manganese and the aluminum in the reaction liquid were each 0.1 ppm or less.

EXAMPLE 6

Reaction conditions:
Reaction temperature: 200° C.
Reaction pressure: 5 MPa
Catalyst: Mn—Zr—Al (prepared in the above-mentioned Catalyst Preparation Example 5)
Catalyst amount: 11.25 mL, LHSV=1 $hr^{-1}$
Reaction starting material: purified palm oil 6.5 $g \cdot hr^{-1}$ and methanol 3.2 $g \cdot hr^{-1}$, the methanol in an amount equal to 4.5 times the theoretically needed amount was supplied relative to palm oil.

Figure 9:
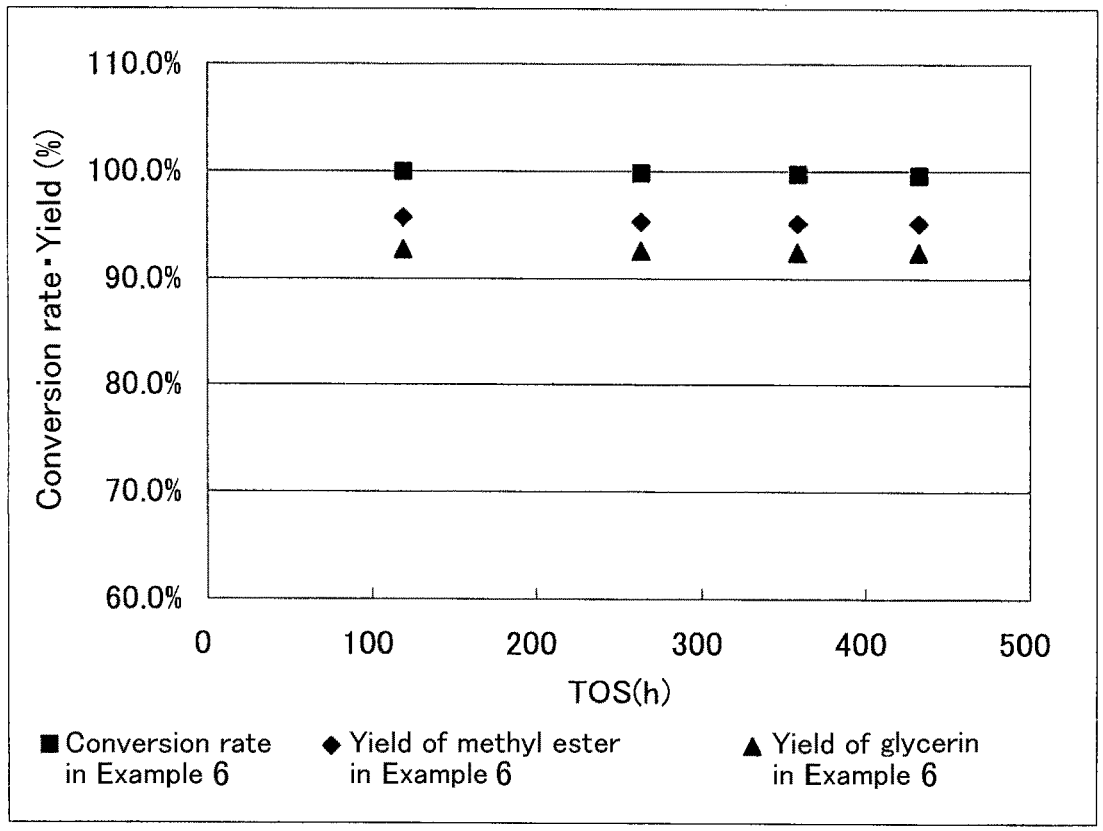
FIG. 9 is a chart showing a variation in a conversion rate of palm oil, a yield of methyl ester, and a yield of glycerin in Example 6.

The reaction liquid was sampled after 119 hours, 263 hour 359 hours, and 433 hours since the start of the reaction. As a result, no reduction was observed in a conversion rate of the palm oil, a yield of methyl ester, and a yield of glycerin even after 430 hours from the start of the reaction. FIG. 9 is a chart showing a variation in a conversion rate of palm oil, a yield of methyl ester, and a yield of glycerin in Example 6.

EXAMPLE 7

Reaction conditions:
Reaction temperature: 200° C.
Reaction pressure: 5 MPa
Catalyst: Mn—Si—Al (prepared in the above-mentioned Catalyst Preparation Example 6)
Catalyst amount: 15 mL, LHSV=1 hr$^{-1}$,
Reaction starting material: purified palm oil 6.3 g·hr$^{-1}$ and methanol 6.3 g·hr$^{-1}$, the methanol in an amount equal to 9 times the theoretically needed amount was supplied relative to palm oil.

Figure 10:
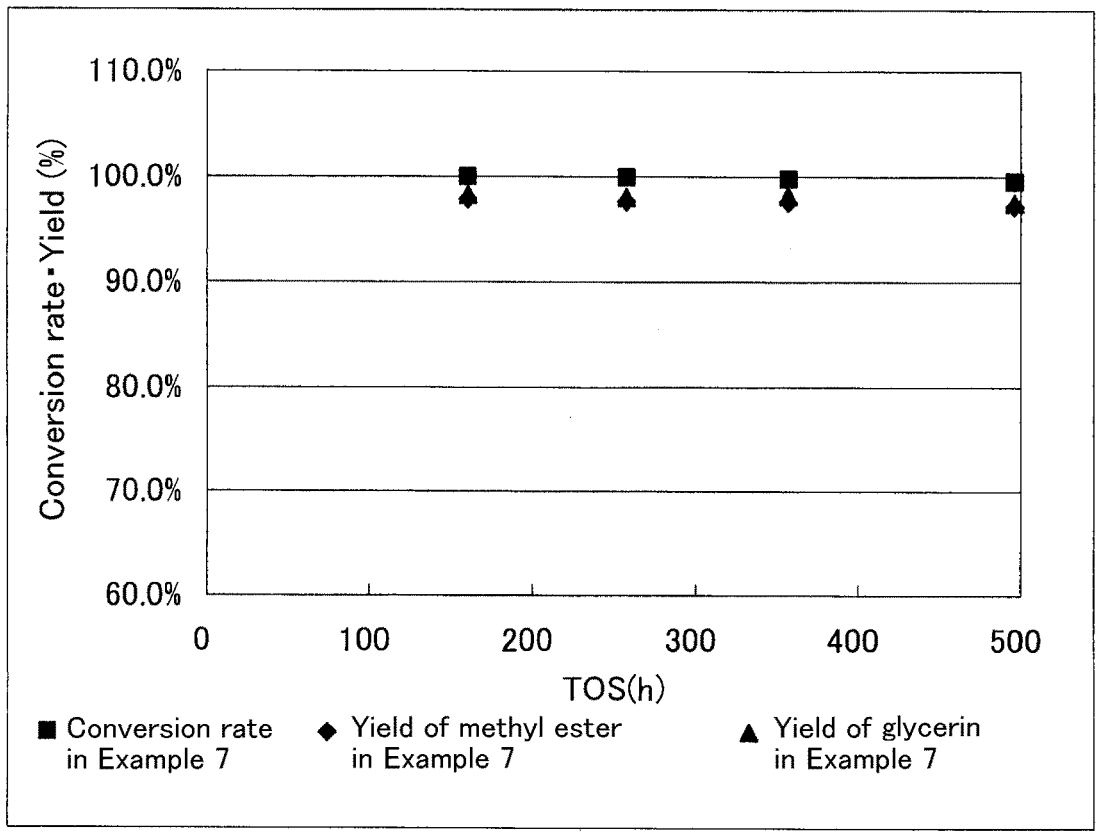
FIG. 10 is a chart showing a variation in a conversion rate of palm oil, a yield of methyl ester, and a yield of glycerin in Example 7.

The reaction liquid was sampled after 160 hours, 257 hours, 357 hours, and 497 hours since the start of the reaction. As a result, no reduction was observed in a conversion rate of the palm oil, a yield of methyl ester, and a yield of glycerin even after 497 hours from the start of the reaction. FIG. 10 is a chart showing a variation in a conversion rate of palm oil, a yield of methyl ester, and a yield of glycerin in Example 7.

EXAMPLE 8

Figure 11:
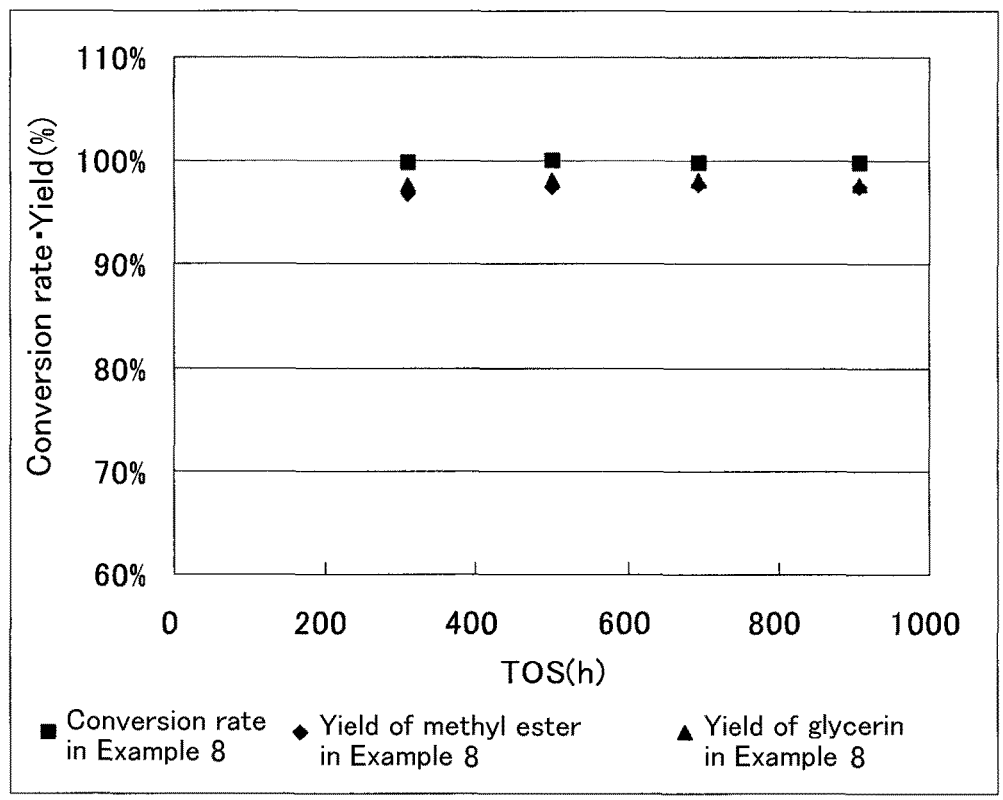
FIG. 11 is a chart showing a variation in a conversion rate of palm oil, a yield of methyl ester, and a yield of glycerin in Example 8.

The reaction was performed in the same manner as in Example 1, except that the catalyst which had been prepared in Catalyst Preparation Example 2 was used and the catalyst amount was as follows: 7.5 mL, LHSV=2 hr$^{-1}$. FIG. 11 shows a variation over a period of 1000 hours from the start of the reaction in a conversion rate of palm oil, a yield of methyl ester, and a yield of glycerin.

EXAMPLE 9

Figure 12:
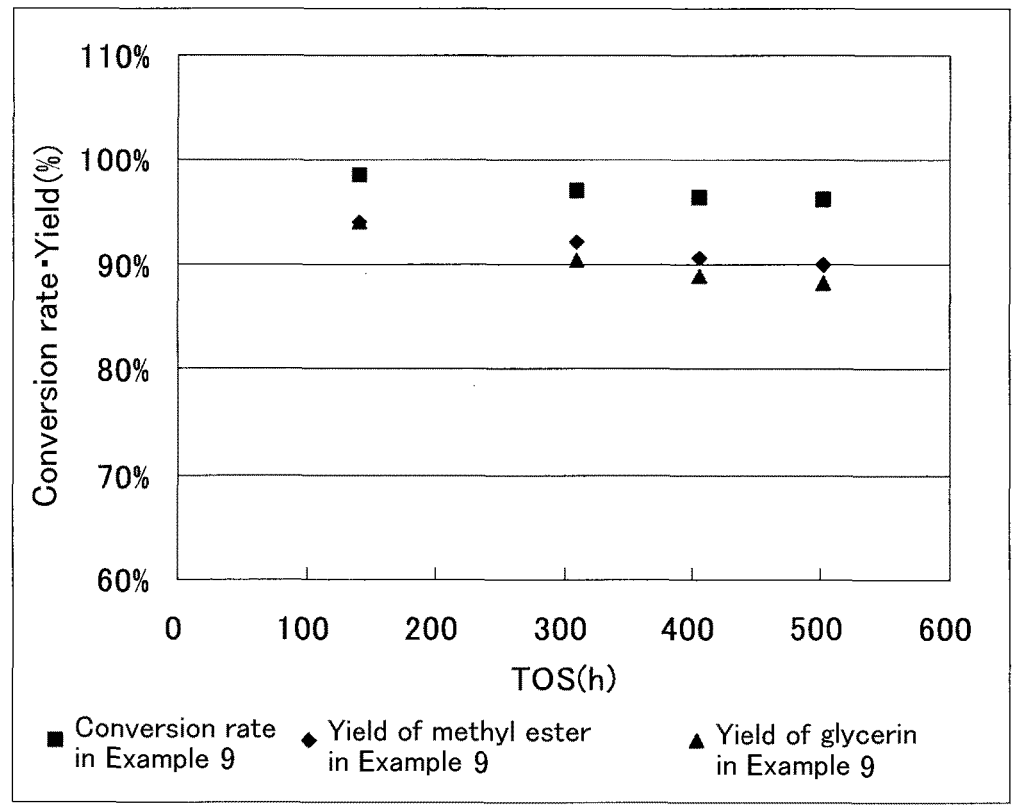
FIG. 12 is a chart showing a variation in a conversion rate of palm oil, a yield of methyl ester, and a yield of glycerin in Example 9.

The reaction was performed in the same manner as in Example 1, except that the catalyst which had been prepared in Catalyst Preparation Example 6 was used and the catalyst amount was as follows: 7.5 mL, LHSV=2 hr$^{-1}$. FIG. 12 shows a variation over a period of 600 hours from the start of the reaction in a conversion rate of palm oil, a yield of methyl ester, and a yield of glycerin.

EXAMPLE 10

Figure 13:
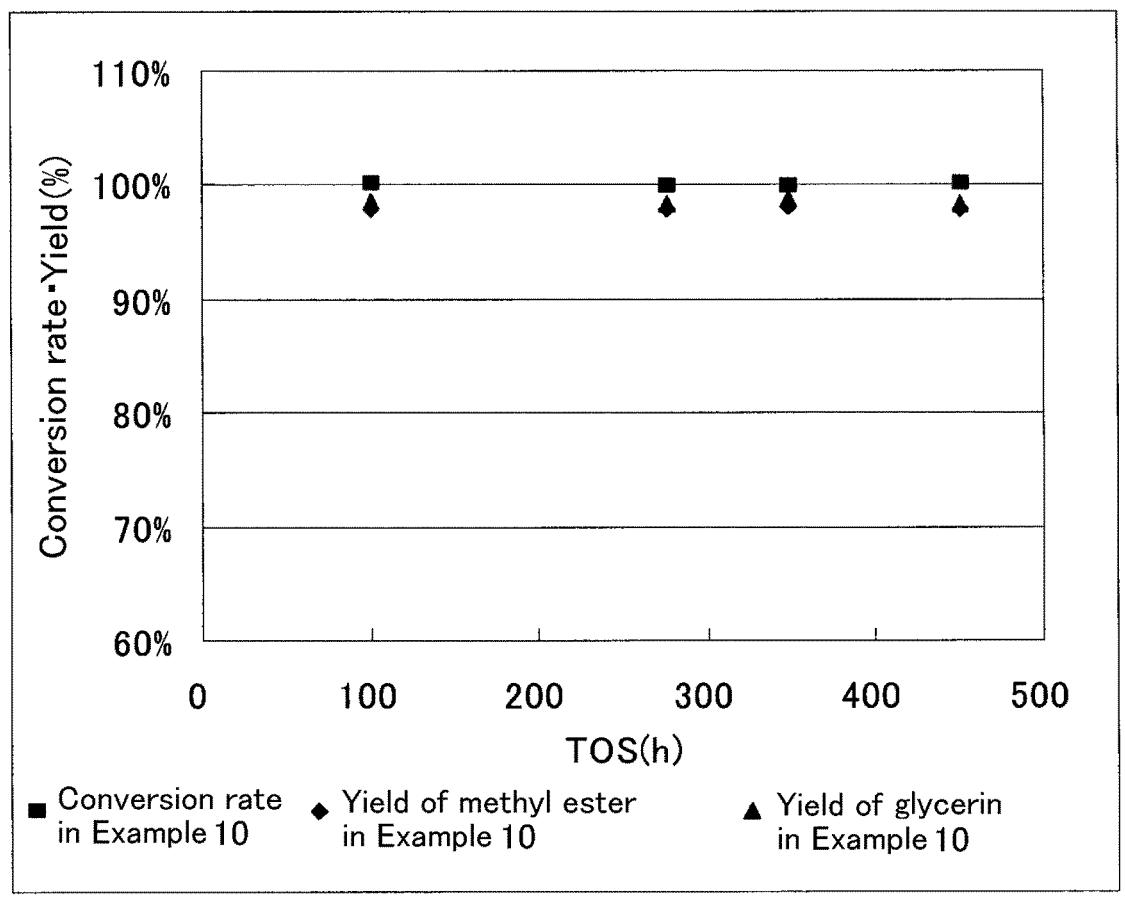
FIG. 13 is a chart showing a variation in a conversion rate of palm oil, a yield of methyl ester, and a yield of glycerin in Example 10.

The reaction was performed in the same manner as in Example 1, except that the catalyst which had been prepared in Catalyst Preparation Example 7 was used as the catalyst. FIG. 13 shows a variation over a period of 500 hours from the start of the reaction in a conversion rate of palm oil, a yield of methyl ester, and a yield of glycerin.

REFERENCE EXAMPLE 1

The following reaction was performed using the catalyst which had been prepared in Catalyst Preparation Reference Example 1 [Mn$_x$Al$_{1-x}$(OH)$_2$][(NO$_3$)$_{1-x}$·yH$_2$O]. Palm oil 58.45 g, palmitic acid 3.08 g, methanol 20 g, and the catalyst 2.5 g prepared in Catalyst Preparation Reference Example 1 were charged into a 200 mL autoclave. After nitrogen substitution, the reaction was allowed to proceed at a reaction temperature of 200° C. for 3 hours under internal stirring. The conversion rate of the palm oil was 100 mol %, but the catalyst could not be recovered because it was leached into the reaction liquid.

COMPARATIVE EXAMPLE 1

The reaction was performed in the same manner as in Example 1, except that the catalyst which had been prepared in Catalyst Preparation Comparative Example 1 was used as the catalyst. The conversion rate of palm oil was 25%; the yield of methyl ester was 2%; and the yield of glycerin was 0%, after 100 hours since the start of the reaction.

This result shows that if the catalyst (Mn—P) which is a composite oxide and/or a mixed oxide of a manganese compound and a pentavalent nonmetal is used, the reaction hardly proceeds.

The invention claimed is:

1. A method for producing fatty acid alkyl esters and/or glycerin,
the method comprising a step of bringing a fat or oil into contact with an alcohol in the presence of a catalyst,
wherein the catalyst includes a manganese element and a trivalent metal element, and wherein the catalyst is prepared by calcination at 600° C. or more.

2. The method for producing fatty acid alkyl esters and/or glycerin according to claim 1, wherein the trivalent metal element is an oxide of the trivalent metal element.

3. The method for producing fatty acid alkyl esters and/or glycerin according to claim 2, wherein the oxide of the trivalent metal element is an aluminum oxide.

4. The method for producing fatty acid alkyl esters and/or glycerin according to claim 1,
wherein the manganese element is a manganese oxide.

5. The method for producing fatty acid alkyl esters and/or glycerin according to claim 1,
wherein the catalyst is a mixed oxide and/or a composite oxide of a manganese oxide and an aluminum oxide.

6. A catalyst for producing fatty acid alkyl esters and/or glycerin, used in the method for producing fatty acid alkyl esters and/or glycerin of claim 1.

7. The method for producing fatty acid alkyl esters and/or glycerin according to claim 2,
wherein the manganese element is a manganese oxide.

8. The method for producing fatty acid alkyl esters and/or glycerin according to claim 3,
wherein the manganese element is a manganese oxide.

9. The method for producing fatty acid alkyl esters and/or glycerin according to claim 2,
wherein the catalyst is a mixed oxide and/or a composite oxide of a manganese oxide and an aluminum oxide.

10. The method for producing fatty acid alkyl esters and/or glycerin according to claim 3,
wherein the catalyst is a mixed oxide and/or a composite oxide of a manganese oxide and an aluminum oxide.

11. The method for producing fatty acid alkyl esters and/or glycerin according to claim 4,
wherein the catalyst is a mixed oxide and/or a composite oxide of a manganese oxide and an aluminum oxide.

12. The method for producing fatty acid alkyl esters and/or glycerin according to claim 7,
wherein the catalyst is a mixed oxide and/or a composite oxide of a manganese oxide and an aluminum oxide.

13. The method for producing fatty acid alkyl esters and/or glycerin according to claim 8,
wherein the catalyst is a mixed oxide and/or a composite oxide of a manganese oxide and an aluminum oxide.

14. A catalyst for producing fatty acid alkyl esters and/or glycerin, used in the method for producing fatty acid alkyl esters and/or glycerin of claim 2.

15. A catalyst for producing fatty acid alkyl esters and/or glycerin, used in the method for producing fatty acid alkyl esters and/or glycerin of claim 3.

16. A catalyst for producing fatty acid alkyl esters and/or glycerin, used in the method for producing fatty acid alkyl esters and/or glycerin of claim 4.

17. A catalyst for producing fatty acid alkyl esters and/or glycerin, used in the method for producing fatty acid alkyl esters and/or glycerin of claim 5.

18. A catalyst for producing fatty acid alkyl esters and/or glycerin, used in the method for producing fatty acid alkyl esters and/or glycerin of claim 7.

19. A catalyst for producing fatty acid alkyl esters and/or glycerin, used in the method for producing fatty acid alkyl esters and/or glycerin of claim 8.

20. A catalyst for producing fatty acid alkyl esters and/or glycerin, used in the method for producing fatty acid alkyl esters and/or glycerin of claim 9.

21. The method for producing fatty acid alkyl esters and/or glycerin according to claim 1, wherein a phase separation is carried out after evaporating the alcohol from a reaction mixture in the absence of the catalyst.

22. The method for producing fatty acid alkyl esters and/or glycerin according to claim 1, wherein a phase separation is carried out after evaporating the alcohol from a reaction mixture in the condition that the reaction mixture has 1000 ppm or less of a total concentration of active metal components leached from the catalyst.

23. The method for producing fatty acid alkyl esters and/or glycerin according to claim 1, wherein the fats and oils are subjected to a degumming step before the step of bringing the fat or oil into contact with the alcohol.

24. The method for producing fatty acid alkyl esters and/or glycerin according to claim 1, wherein the step of bringing the fat or oil into contact with the alcohol is carried out at the temperature from 150° C. to 235° C.

25. The method for producing fatty acid alkyl esters and/or glycerin according to claim 1, wherein the step of bringing the fat or oil into contact with the alcohol is carried out by a fixed bed flow system.

* * * * *

UNITED STATES PATENT AND TRADEMARK OFFICE
CERTIFICATE OF CORRECTION

| | |
|---|---|
| PATENT NO. | : 8,093,416 B2 |
| APPLICATION NO. | : 12/744235 |
| DATED | : January 10, 2012 |
| INVENTOR(S) | : Takeo Akatsuka et al. |

It is certified that error appears in the above-identified patent and that said Letters Patent is hereby corrected as shown below:

Claim 23, at column 22, line 6, please amend "the fats and oils" to read "the fat and oil".

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,093,416 B2 |
| APPLICATION NO. | : 12/744235 |
| DATED | : January 10, 2012 |
| INVENTOR(S) | : Takeo Akatsuka et al. |

It is certified that error appears in the above-identified patent and that said Letters Patent is hereby corrected as shown below:

Claim 23, at column 22, line 6, please amend "the fats and oils" to read "the fat or oil".

This certificate supersedes the Certificate of Correction issued May 8, 2012.

Signed and Sealed this
Fourteenth Day of August, 2012

David J. Kappos
*Director of the United States Patent and Trademark Office*